(12) United States Patent
Arne et al.

(10) Patent No.: US 8,718,193 B2
(45) Date of Patent: May 6, 2014

(54) ACTIVE SIGNAL PROCESSING PERSONAL HEALTH SIGNAL RECEIVERS

(75) Inventors: Lawrence Arne, Redwood City, CA (US); KitYee Au-Yeung, San Francisco, CA (US); Kenneth C. Crandall, Sunnyvale, CA (US); Timothy Robertson, Belmont, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 747 days.

(21) Appl. No.: 12/515,527

(22) PCT Filed: Nov. 19, 2007

(86) PCT No.: PCT/US2007/024225
§ 371 (c)(1),
(2), (4) Date: Mar. 3, 2010

(87) PCT Pub. No.: WO2008/063626
PCT Pub. Date: May 29, 2008

(65) Prior Publication Data
US 2010/0316158 A1    Dec. 16, 2010

Related U.S. Application Data

(60) Provisional application No. 60/866,581, filed on Nov. 20, 2006, provisional application No. 60/945,251, filed on Jun. 20, 2007.

(51) Int. Cl.
*H04L 27/00* (2006.01)
(52) U.S. Cl.
USPC ........... 375/316; 375/344; 375/285; 600/300; 607/60

(58) Field of Classification Search
USPC ............................. 375/316; 600/300; 607/60
See application file for complete search history.

(56) References Cited

U.S. PATENT DOCUMENTS

| | | | |
|---|---|---|---|
| 3,607,788 A | 9/1971 | Adolph | |
| 3,642,008 A | 2/1972 | Bolduc | |

(Continued)

FOREIGN PATENT DOCUMENTS

| | | |
|---|---|---|
| CN | 1991868 | 7/2007 |
| CN | 101005470 | 7/2007 |

(Continued)

OTHER PUBLICATIONS

"PALO Bluetooth Baseband" PALO Bluetooth Resource Center (2002) Retrieved from internet Dec. 12, 2012 at URL: http://palowireless.com/bluearticles/baseband.asp; first cited in Office Action dated Jan. 17, 2013 for EP08853901.0.

(Continued)

*Primary Examiner* — Siu Lee
(74) *Attorney, Agent, or Firm* — Bret E. Field; Bozicevic, Field & Francis, LLP

(57) ABSTRACT

The invention provides a receiver associated with a body, e.g., located inside or within close proximity to a body, configured to receive and decode a signal from an in vivo transmitter which located inside the body. Signal receivers of the invention provide for accurate signal decoding of a low-level signal, even in the presence of significant noise, using a small-scale chip, e.g., where the chip consumes very low power. Also provided are systems that include the receivers, as well as methods of using the same.

3 Claims, 12 Drawing Sheets

(56) References Cited

U.S. PATENT DOCUMENTS

| | | |
|---|---|---|
| 3,679,480 A | 7/1972 | Brown et al. |
| 3,682,160 A | 8/1972 | Murata |
| 3,719,183 A | 3/1973 | Schwartz |
| 3,828,766 A | 8/1974 | Krasnow |
| 3,837,339 A | 9/1974 | Aisenberg et al. |
| 3,893,111 A | 7/1975 | Cotter |
| 3,944,064 A | 3/1976 | Bashaw et al. |
| 3,967,202 A | 6/1976 | Batz |
| 3,978,407 A * | 8/1976 | Forney et al. ............... 375/231 |
| 3,989,050 A | 11/1976 | Buchalter |
| 4,017,856 A | 4/1977 | Wiegand |
| 4,055,178 A | 10/1977 | Harrigan |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,559,950 A | 12/1985 | Vaughan |
| 4,564,363 A | 1/1986 | Bagnall et al. |
| 4,635,641 A | 1/1987 | Hoffman |
| 4,654,165 A | 3/1987 | Eisenber |
| 4,669,479 A | 6/1987 | Dunseath |
| 4,681,111 A | 7/1987 | Silvian |
| 4,687,660 A | 8/1987 | Baker et al. |
| 4,725,997 A | 2/1988 | Urquhart et al. |
| 4,763,659 A | 8/1988 | Dunseath |
| 4,784,162 A | 11/1988 | Ricks |
| 4,793,825 A | 12/1988 | Benjamin et al. |
| 4,844,076 A | 7/1989 | Lesho |
| 4,871,974 A * | 10/1989 | Davis et al. ............... 329/345 |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,016,634 A | 5/1991 | Vock et al. |
| 5,079,006 A | 1/1992 | Urquhart |
| 5,167,626 A | 12/1992 | Casper |
| 5,176,626 A | 1/1993 | Soehendra |
| 5,179,578 A * | 1/1993 | Ishizu ............... 375/332 |
| 5,261,402 A | 11/1993 | DiSabito |
| 5,263,481 A | 11/1993 | Axelgaard et al. |
| 5,279,607 A | 1/1994 | Schentag et al. |
| 5,281,287 A | 1/1994 | Lloyd |
| 5,283,136 A | 2/1994 | Peled et al. |
| 5,305,745 A | 4/1994 | Zacouto |
| 5,318,557 A | 6/1994 | Gross |
| 5,394,882 A | 3/1995 | Mawhinney |
| 5,395,366 A | 3/1995 | D'Andrea et al. |
| 5,458,141 A | 10/1995 | Neil et al. |
| 5,485,841 A | 1/1996 | Watkin et al. |
| 5,511,548 A | 4/1996 | Riazzi et al. |
| 5,596,302 A | 1/1997 | Mastrocola et al. |
| 5,600,548 A | 2/1997 | Nguyen et al. |
| 5,634,468 A | 6/1997 | Platt |
| 5,645,063 A | 7/1997 | Straka et al. |
| 5,720,771 A | 2/1998 | Snell |
| 5,740,811 A | 4/1998 | Hedberg |
| 5,757,326 A | 5/1998 | Koyama et al. |
| 5,792,048 A | 8/1998 | Schaefer |
| 5,802,467 A | 9/1998 | Salazar |
| 5,833,716 A | 11/1998 | Bar-Or |
| 5,845,265 A | 12/1998 | Woolston |
| 5,862,803 A | 1/1999 | Besson |
| 5,868,136 A | 2/1999 | Fox |
| 5,921,925 A | 7/1999 | Cartmell et al. |
| 5,925,030 A | 7/1999 | Gross et al. |
| 5,957,854 A | 9/1999 | Besson |
| 5,963,132 A | 10/1999 | Yoakum et al. |
| 5,974,124 A | 10/1999 | Schlueter, Jr. et al. |
| 5,999,846 A | 12/1999 | Pardey et al. |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach et al. |
| 6,081,734 A | 6/2000 | Batz |
| 6,083,248 A | 7/2000 | Thompson |
| 6,095,985 A | 8/2000 | Raymond et al. |
| 6,122,351 A | 9/2000 | Schlueter, Jr. et al. |
| 6,141,592 A | 10/2000 | Pauly |
| 6,200,265 B1 | 3/2001 | Walsh et al. |
| 6,200,625 B1 | 3/2001 | Beckett |
| 6,204,764 B1 | 3/2001 | Maloney |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,275,476 B1 | 8/2001 | Wood |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson |
| 6,315,719 B1 | 11/2001 | Rode et al. |
| 6,358,202 B1 | 3/2002 | Arent |
| 6,364,834 B1 | 4/2002 | Reuss |
| 6,366,206 B1 | 4/2002 | Ishikawa et al. |
| 6,371,927 B1 | 4/2002 | Brune |
| 6,374,670 B1 | 4/2002 | Spelman |
| 6,380,858 B1 | 4/2002 | Yarin et al. |
| 6,394,997 B1 | 5/2002 | Lemelson |
| 6,409,674 B1 | 6/2002 | Brockway et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,496,705 B1 | 12/2002 | Ng et al. |
| 6,526,315 B1 | 2/2003 | Inagawa |
| 6,544,174 B2 | 4/2003 | West |
| 6,564,079 B1 | 5/2003 | Cory |
| 6,574,425 B1 * | 6/2003 | Weiss et al. ............... 356/402 |
| 6,577,893 B1 | 6/2003 | Besson |
| 6,579,231 B1 | 6/2003 | Phipps |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,800,060 B2 | 10/2004 | Marshall |
| 6,801,137 B2 | 10/2004 | Eggers et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |

(56) References Cited

U.S. PATENT DOCUMENTS

| | | | |
|---|---|---|---|
| 6,909,878 | B2 | 6/2005 | Haller |
| 6,922,592 | B2 | 7/2005 | Thompson et al. |
| 6,928,370 | B2 | 8/2005 | Anuzis et al. |
| 6,929,636 | B1 | 8/2005 | Von Alten |
| 6,937,150 | B2 | 8/2005 | Medema |
| 6,942,616 | B2 | 9/2005 | Kerr |
| 6,951,536 | B2 | 10/2005 | Yokoi |
| 6,957,107 | B2 | 10/2005 | Rogers et al. |
| 6,968,153 | B1 | 11/2005 | Heinonen |
| 6,987,965 | B2 | 1/2006 | Ng et al. |
| 6,990,082 | B1 | 1/2006 | Zehavi et al. |
| 7,002,476 | B2 | 2/2006 | Rapchak |
| 7,004,395 | B2 | 2/2006 | Koenck |
| 7,009,634 | B2 | 3/2006 | Iddan et al. |
| 7,009,946 | B1 | 3/2006 | Kardach |
| 7,013,162 | B2 | 3/2006 | Gorsuch |
| 7,016,648 | B2 | 3/2006 | Haller |
| 7,020,508 | B2 | 3/2006 | Stivoric |
| 7,024,248 | B2 | 4/2006 | Penner et al. |
| 7,031,745 | B2 | 4/2006 | Shen |
| 7,031,857 | B2 | 4/2006 | Tarassenko et al. |
| 7,039,453 | B2 | 5/2006 | Mullick |
| 7,046,649 | B2 | 5/2006 | Awater et al. |
| 7,118,531 | B2 | 10/2006 | Krill |
| 7,127,300 | B2 | 10/2006 | Mazar et al. |
| 7,146,228 | B2 | 12/2006 | Nielsen |
| 7,146,449 | B2 | 12/2006 | Do et al. |
| 7,149,581 | B2 | 12/2006 | Goedeke et al. |
| 7,154,071 | B2 | 12/2006 | Sattler et al. |
| 7,155,232 | B2 | 12/2006 | Godfrey et al. |
| 7,160,258 | B2 | 1/2007 | Imran |
| 7,164,942 | B2 | 1/2007 | Avrahami |
| 7,171,166 | B2 | 1/2007 | Ng et al. |
| 7,171,177 | B2 | 1/2007 | Park et al. |
| 7,171,259 | B2 | 1/2007 | Rytky |
| 7,176,784 | B2 | 2/2007 | Gilbert et al. |
| 7,187,960 | B2 | 3/2007 | Abreu |
| 7,188,767 | B2 | 3/2007 | Penuela |
| 7,194,038 | B1 | 3/2007 | Inkinen |
| 7,206,630 | B1 | 4/2007 | Tarler |
| 7,209,790 | B2 | 4/2007 | Thompson et al. |
| 7,215,660 | B2 | 5/2007 | Perlman |
| 7,215,991 | B2 | 5/2007 | Besson |
| 7,218,967 | B2 | 5/2007 | Bergelson |
| 7,231,451 | B2 | 6/2007 | Law |
| 7,243,118 | B2 | 7/2007 | Lou |
| 7,246,521 | B2 | 7/2007 | Kim |
| 7,249,212 | B2 | 7/2007 | Do |
| 7,252,792 | B2 | 8/2007 | Perrault |
| 7,253,716 | B2 | 8/2007 | Lovoi et al. |
| 7,261,690 | B2 | 8/2007 | Teller |
| 7,270,633 | B1 | 9/2007 | Goscha |
| 7,273,454 | B2 | 9/2007 | Raymond et al. |
| 7,289,855 | B2 | 10/2007 | Nghiem |
| 7,291,497 | B2 | 11/2007 | Holmes |
| 7,292,139 | B2 | 11/2007 | Mazar et al. |
| 7,294,105 | B1 | 11/2007 | Islam |
| 7,313,163 | B2 | 12/2007 | Liu |
| 7,317,378 | B2 | 1/2008 | Jarvis et al. |
| 7,318,808 | B2 | 1/2008 | Tarassenko et al. |
| 7,336,929 | B2 | 2/2008 | Yasuda |
| 7,342,895 | B2 | 3/2008 | Serpa |
| 7,346,380 | B2 | 3/2008 | Axelgaard et al. |
| 7,349,722 | B2 | 3/2008 | Witkowski et al. |
| 7,352,998 | B2 | 4/2008 | Palin |
| 7,353,258 | B2 | 4/2008 | Washburn |
| 7,357,891 | B2 | 4/2008 | Yang et al. |
| 7,359,674 | B2 | 4/2008 | Markki |
| 7,366,558 | B2 | 4/2008 | Virtanen et al. |
| 7,373,196 | B2 | 5/2008 | Ryu et al. |
| 7,375,739 | B2 | 5/2008 | Robbins |
| 7,376,435 | B2 | 5/2008 | McGowan |
| 7,382,263 | B2 | 6/2008 | Danowski et al. |
| 7,387,607 | B2 | 6/2008 | Holt |
| 7,388,903 | B2 | 6/2008 | Godfrey et al. |
| 7,389,088 | B2 | 6/2008 | Kim |
| 7,392,015 | B1 | 6/2008 | Farlow |
| 7,395,106 | B2 | 7/2008 | Ryu et al. |
| 7,396,330 | B2 | 7/2008 | Banet |
| 7,404,968 | B2 | 7/2008 | Abrams et al. |
| 7,413,544 | B2 | 8/2008 | Kerr |
| 7,414,534 | B1 | 8/2008 | Kroll et al. |
| 7,414,543 | B2 | 8/2008 | Rye et al. |
| 7,415,242 | B1 | 8/2008 | Ngan |
| 7,424,268 | B2 | 9/2008 | Diener |
| 7,424,319 | B2 | 9/2008 | Muehlsteff |
| 7,427,266 | B2 | 9/2008 | Ayer et al. |
| 7,430,257 | B1* | 9/2008 | Shattil ............... 375/347 |
| 7,434,146 | B1* | 10/2008 | Verdu et al. ............ 714/780 |
| 7,471,665 | B2 | 12/2008 | Perlman |
| 7,499,674 | B2 | 3/2009 | Salokannel |
| 7,502,643 | B2 | 3/2009 | Farringdon et al. |
| 7,510,121 | B2 | 3/2009 | Koenck |
| 7,512,448 | B2 | 3/2009 | Malick |
| 7,515,043 | B2 | 4/2009 | Welch |
| 7,519,416 | B2 | 4/2009 | Sula et al. |
| 7,523,756 | B2 | 4/2009 | Minai |
| 7,525,426 | B2 | 4/2009 | Edelstein |
| 7,539,533 | B2 | 5/2009 | Tran |
| 7,542,878 | B2 | 6/2009 | Nanikashvili |
| 7,551,590 | B2 | 6/2009 | Haller |
| 7,554,452 | B2 | 6/2009 | Cole |
| 7,575,005 | B2 | 8/2009 | Mumford |
| 7,616,111 | B2 | 11/2009 | Covannon |
| 7,616,710 | B2* | 11/2009 | Kim et al. ............ 375/334 |
| 7,617,001 | B2 | 11/2009 | Penner et al. |
| 7,639,473 | B2 | 12/2009 | Hsu et al. |
| 7,640,802 | B2 | 1/2010 | King et al. |
| 7,647,112 | B2 | 1/2010 | Tracey |
| 7,647,185 | B2 | 1/2010 | Tarassenko et al. |
| 7,653,031 | B2 | 1/2010 | Godfrey et al. |
| 7,672,714 | B2 | 3/2010 | Kuo |
| 7,673,679 | B2 | 3/2010 | Harrison et al. |
| 7,678,043 | B2 | 3/2010 | Gilad |
| 7,697,994 | B2 | 4/2010 | VanDanacker et al. |
| 7,720,036 | B2 | 5/2010 | Sadri |
| 7,729,776 | B2 | 6/2010 | Von Arx et al. |
| 7,733,224 | B2 | 6/2010 | Tran |
| 7,736,318 | B2 | 6/2010 | Costentino |
| 7,756,587 | B2 | 7/2010 | Penner et al. |
| 7,779,614 | B1 | 8/2010 | McGonagle et al. |
| 7,796,043 | B2 | 9/2010 | Euliano et al. |
| 7,797,033 | B2 | 9/2010 | D'Andrea et al. |
| 7,809,399 | B2 | 10/2010 | Lu |
| 7,844,341 | B2 | 11/2010 | Von Arx et al. |
| 7,904,133 | B2 | 3/2011 | Gehman et al. |
| 8,025,149 | B2 | 9/2011 | Sterry et al. |
| 8,073,707 | B2 | 12/2011 | Teller et al. |
| 8,083,128 | B2 | 12/2011 | Dembo et al. |
| 8,123,576 | B2 | 2/2012 | Kim |
| 8,170,515 | B2 | 5/2012 | Le Reverend et al. |
| 8,180,425 | B2 | 5/2012 | Selvitelli et al. |
| 8,200,320 | B2 | 6/2012 | Kovacs |
| 8,214,007 | B2 | 7/2012 | Baker et al. |
| 8,238,998 | B2 | 8/2012 | Park |
| 8,249,686 | B2 | 8/2012 | Libbus et al. |
| 8,258,962 | B2 | 9/2012 | Robertson et al. |
| 8,285,356 | B2 | 10/2012 | Bly et al. |
| 8,290,574 | B2 | 10/2012 | Felid et al. |
| 8,301,232 | B2 | 10/2012 | Albert et al. |
| 8,308,640 | B2 | 11/2012 | Baldus et al. |
| 8,315,687 | B2 | 11/2012 | Cross et al. |
| 8,369,936 | B2 | 2/2013 | Farringdon et al. |
| 8,386,009 | B2 | 2/2013 | Lindberg et al. |
| 2001/0027331 | A1 | 10/2001 | Thompson |
| 2001/0044588 | A1 | 11/2001 | Mault |
| 2001/0051766 | A1 | 12/2001 | Gazdinski |
| 2002/0002326 | A1 | 1/2002 | Causey, III |
| 2002/0026111 | A1 | 2/2002 | Ackerman |
| 2002/0032385 | A1 | 3/2002 | Raymond et al. |
| 2002/0040278 | A1 | 4/2002 | Anuzis et al. |
| 2002/0077620 | A1 | 6/2002 | Sweeney et al. |
| 2002/0132226 | A1 | 9/2002 | Nair |
| 2002/0193669 | A1 | 12/2002 | Glukhovsky |

(56) References Cited

U.S. PATENT DOCUMENTS

| | | |
|---|---|---|
| 2002/0193846 A1 | 12/2002 | Pool et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0063522 A1 | 4/2003 | Sagar |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1* | 11/2003 | Ericson et al. .............. 600/561 |
| 2003/0216729 A1 | 11/2003 | Marchitto |
| 2003/0229382 A1 | 12/2003 | Sun et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0111011 A1 | 6/2004 | Uchiyama et al. |
| 2004/0115517 A1 | 6/2004 | Fukuda et al. |
| 2004/0121015 A1 | 6/2004 | Chidlaw et al. |
| 2004/0122297 A1 | 6/2004 | Stahmann et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0171914 A1 | 9/2004 | Avni |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0260154 A1 | 12/2004 | Sidelnik |
| 2004/0267240 A1 | 12/2004 | Gross et al. |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0027330 A1* | 2/2005 | Govari .............. 607/60 |
| 2005/0038321 A1 | 2/2005 | Fujita et al. |
| 2005/0043634 A1 | 2/2005 | Yokoi et al. |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0148883 A1 | 7/2005 | Boesen |
| 2005/0151625 A1 | 7/2005 | Lai |
| 2005/0154428 A1 | 7/2005 | Bruinsma |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0002484 A1* | 1/2006 | Miyazaki et al. .............. 375/259 |
| 2006/0036134 A1 | 2/2006 | Tarassenko et al. |
| 2006/0061472 A1 | 3/2006 | Lovoi et al. |
| 2006/0065713 A1 | 3/2006 | Kingery |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1* | 5/2006 | Bettesh et al. .............. 607/60 |
| 2006/0100533 A1 | 5/2006 | Han |
| 2006/0109058 A1 | 5/2006 | Keating |
| 2006/0110962 A1 | 5/2006 | Powell |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Wolfe |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0247505 A1 | 11/2006 | Siddiqui |
| 2006/0253005 A1 | 11/2006 | Drinan |
| 2006/0255064 A1 | 11/2006 | Donaldson |
| 2006/0268546 A1 | 11/2006 | Hoag |
| 2006/0270346 A1 | 11/2006 | Ibrahim |
| 2006/0273882 A1 | 12/2006 | Posamentier |
| 2006/0280227 A1 | 12/2006 | Pinkney |
| 2006/0282001 A1 | 12/2006 | Noel |
| 2006/0285607 A1* | 12/2006 | Strodtbeck et al. .............. 375/298 |
| 2006/0289640 A1 | 12/2006 | Mercure |
| 2006/0293607 A1 | 12/2006 | Alt |

(56) References Cited

U.S. PATENT DOCUMENTS

| | | |
|---|---|---|
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0287891 A1* | 12/2007 | Horn .................. 600/300 |
| 2007/0299480 A1 | 12/2007 | Hill |
| 2008/0004503 A1* | 1/2008 | Nisani et al. .................. 600/300 |
| 2008/0014866 A1 | 1/2008 | Lipowshi |
| 2008/0015421 A1* | 1/2008 | Penner .................. 600/300 |
| 2008/0015494 A1 | 1/2008 | Santini et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0046038 A1 | 2/2008 | Hill |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemiec et al. |
| 2008/0103440 A1 | 5/2008 | Ferren et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0223936 A1 | 9/2008 | Mickle et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009332 A1 | 1/2009 | Nunez et al. |
| 2009/0024045 A1 | 1/2009 | Prakash |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076397 A1 | 3/2009 | Libbus et al. |
| 2009/0082645 A1 | 3/2009 | Hafezi et al. |
| 2009/0088618 A1 | 4/2009 | Ameson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0135886 A1 | 5/2009 | Robertson et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182212 A1 | 7/2009 | Say et al. |
| 2009/0182213 A1 | 7/2009 | Say et al. |

(56) References Cited

U.S. PATENT DOCUMENTS

| | | |
|---|---|---|
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0277815 A1 | 11/2009 | Kohl et al. |
| 2009/0281539 A1 | 11/2009 | Selig |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0312619 A1 | 12/2009 | Say et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0006585 A1 | 1/2010 | Flowers et al. |
| 2010/0010330 A1 | 1/2010 | Rankers |
| 2010/0033324 A1 | 2/2010 | Shimizu et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0185055 A1 | 7/2010 | Robertson |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0268288 A1* | 10/2010 | Hunter et al. .............. 607/3 |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298730 A1 | 11/2010 | Tarassenko et al. |
| 2010/0299155 A1 | 11/2010 | Findlay et al. |
| 2010/0312188 A1 | 12/2010 | Robertson et al. |
| 2010/0312580 A1 | 12/2010 | Tarassenko et al. |
| 2010/0332443 A1 | 12/2010 | Gartenberg |
| 2011/0009715 A1 | 1/2011 | O'Reilly et al. |
| 2011/0040203 A1 | 2/2011 | Savage et al. |
| 2011/0050431 A1 | 3/2011 | Hood et al. |
| 2011/0054265 A1 | 3/2011 | Hafezi et al. |
| 2011/0144470 A1 | 6/2011 | Mazar et al. |
| 2011/0279963 A1 | 11/2011 | Kumar et al. |
| 2012/0029309 A1 | 2/2012 | Paquet et al. |
| 2012/0101396 A1 | 4/2012 | Solosko et al. |
| 2012/0197144 A1 | 8/2012 | Christ et al. |
| 2012/0265544 A1 | 10/2012 | Hwang et al. |
| 2012/0310070 A1 | 12/2012 | Kumar et al. |
| 2012/0316413 A1 | 12/2012 | Liu et al. |
| 2013/0030259 A1 | 1/2013 | Thomsen et al. |
| 2013/0060115 A1 | 3/2013 | Gehman et al. |

FOREIGN PATENT DOCUMENTS

| | | |
|---|---|---|
| CN | 201076456 | 6/2008 |
| EP | 0344939 | 12/1989 |
| EP | 1246356 | 10/2002 |
| EP | 1534054 | 5/2005 |
| EP | 1702553 | 9/2006 |
| EP | 1789128 | 5/2007 |
| EP | 2143369 | 1/2010 |
| GB | 2432862 | 6/2007 |
| IL | 172917 | 6/2010 |
| JP | 361017949 | 1/1986 |
| JP | 61072712 | 4/1986 |
| JP | 05-228128 | 9/1993 |
| JP | 10-14898 | 1/1998 |
| JP | 2000-506410 | 5/2000 |
| JP | 2002-224053 | 8/2002 |
| JP | 2002263185 | 9/2002 |
| JP | 2002291684 | 10/2002 |
| JP | 2004-7187 | 1/2004 |
| JP | 2004134384 | 4/2004 |
| JP | 2005-073886 | 3/2005 |
| JP | 2005-304880 | 4/2005 |
| JP | 2005-532841 | 11/2005 |
| JP | 2005-532849 | 11/2005 |
| JP | 2006006377 | 1/2006 |

(56) References Cited

FOREIGN PATENT DOCUMENTS

| | | |
|---|---|---|
| JP | 2006509574 | 3/2006 |
| JP | 2006-177699 | 7/2006 |
| JP | 2006-187611 | 7/2006 |
| JP | 2006278091 | 10/2006 |
| JP | 2007-313340 | 12/2007 |
| JP | 2008011865 | 1/2008 |
| JP | 2009-061236 | 3/2009 |
| KR | 20020015907 | 3/2002 |
| KR | 20020061744 | 7/2002 |
| KR | 200609977523 | 7/2006 |
| KR | 927471 | 11/2009 |
| TW | 553735 | 9/2003 |
| TW | 200724094 | 7/2007 |
| WO | 8802237 | 4/1988 |
| WO | WO8802237 | 4/1988 |
| WO | WO9308734 | 5/1993 |
| WO | WO9319667 | 10/1993 |
| WO | WO9739963 | 10/1997 |
| WO | WO9843537 | 10/1998 |
| WO | WO9937290 | 7/1999 |
| WO | WO9959465 | 11/1999 |
| WO | WO0033246 | 6/2000 |
| WO | WO 0147466 | 7/2001 |
| WO | WO0149364 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO02095351 | 11/2002 |
| WO | WO03050643 | 6/2003 |
| WO | WO2004014225 | 2/2004 |
| WO | WO2004039256 | 5/2004 |
| WO | WO2004059551 | 7/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2005011237 | 2/2005 |
| WO | WO 2005020023 | 3/2005 |
| WO | WO2005024687 | 3/2005 |
| WO | WO2005047837 | 5/2005 |
| WO | WO2005051166 | 6/2005 |
| WO | WO2005082436 | 9/2005 |
| WO | WO2005110238 | 11/2005 |
| WO | WO2006021932 | 3/2006 |
| WO | WO2006027586 | 3/2006 |
| WO | WO2006035351 | 4/2006 |
| WO | WO2006046648 | 5/2006 |
| WO | WO 2006055892 | 5/2006 |
| WO | WO 2006055956 | 5/2006 |
| WO | WO2006075016 | 7/2006 |
| WO | WO2006100620 | 9/2006 |
| WO | WO 2006104843 | 10/2006 |
| WO | WO2006109072 | 10/2006 |
| WO | WO 2006116718 | 11/2006 |
| WO | WO2006119345 | 11/2006 |
| WO | WO 2006127355 | 11/2006 |
| WO | WO 2007001724 | 1/2007 |
| WO | WO 2007001742 | 1/2007 |
| WO | WO 2007013952 | 2/2007 |
| WO | WO 2007014084 | 2/2007 |
| WO | WO2007014527 | 2/2007 |
| WO | WO 2007021496 | 2/2007 |
| WO | WO 2007027660 | 3/2007 |
| WO | WO 2007028035 | 3/2007 |
| WO | WO2007028035 | 3/2007 |
| WO | 2007036741 | 4/2007 |
| WO | 2007036746 | 4/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO 2007130491 | 11/2007 |
| WO | WO2007133526 | 11/2007 |
| WO | WO2007143535 | 12/2007 |
| WO | WO 2007149546 | 12/2007 |
| WO | WO 2008008281 | 1/2008 |
| WO | WO2008030482 | 3/2008 |
| WO | WO 2008052136 | 5/2008 |
| WO | WO 2008063626 | 5/2008 |
| WO | WO 2008066617 | 6/2008 |
| WO | WO2008076464 | 6/2008 |
| WO | WO2008089232 | 7/2008 |
| WO | WO2008091683 | 7/2008 |
| WO | WO 2008095183 | 8/2008 |
| WO | WO2008097652 | 8/2008 |
| WO | WO 2008101107 | 8/2008 |
| WO | WO 2008112577 | 9/2008 |
| WO | WO 2008112578 | 9/2008 |
| WO | 2008120156 | 10/2008 |
| WO | WO2008133394 | 11/2008 |
| WO | WO2008134185 | 11/2008 |
| WO | 2009001108 | 12/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | 2010019778 | 2/2010 |
| WO | 2010057049 | 5/2010 |
| WO | WO2010080765 | 7/2010 |
| WO | WO2010080843 | 7/2010 |
| WO | WO2010107563 | 9/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | W02012104657 | 8/2012 |
| WO | WO2012158190 | 11/2012 |

OTHER PUBLICATIONS

Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.

Lin et al., "Do Physiological Data Relate to Traditional Usability Indexes?" Proceedings of OZCHI 2005, Canberra, Australia (2005) 10 pp.

Mandryk et al., "A physiological approach for continuously modeling user emotion in interactive play environments" Proceedings of Measuring Behavior (2008) (Maastrichtm The Netherlandsm Aug. 26-29) 2 pp.

Mandryk et al., "Objectively Evaluating Entertainment Technology" Simon Fraser University; CHI (2004) ACM 1-58113-703-6/04/0004; 2 pp.

(56) References Cited

OTHER PUBLICATIONS

Barrie, Heidelberg pH capsule gastric analysis. Texbook of Natural Medicine, (1992), Pizzorno, Murray & Barrie.

Carlson et al., "Evaluation of a non-invasive respiratory monitoring system for sleeping subjects" Physiological Measurement (1999) 20(1): 53.

Heydari et al., "Analysis of the PLL jitter due to power/ground and substrate noise"; IEEE Transactions on Circuits and Systems (2004) 51(12): 2404-16.

Intromedic, MicroCam Innovative Capsule Endoscope Pamphlet. 8 pp (http://www.intromedic.com/en/product/productinfo.asp).

Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.

Mackay et al., "Endoradiosonde" Nature, (1957) 1239-1240, 179 Nature Publishing Group.

McKenzie et al., "Validation of a new telemetric core temperature monitor" J. Therm. Biol. (2004) 29(7-8):605-11.

MiniMitter Co. Inc. "Actiheart" Traditional 510(k) Summary. Sep. 27, 2005.

MiniMitter Co. Inc. Noninvasive technology to help your studies succeed. Mini Mitter.com Mar. 31, 2009.

Mini Mitter Co, Inc. 510(k) Premarket Notification Mini-Logger for Diagnostic Spirometer. Sep. 21, 1999.

Mini Mitter Co, Inc. 510(k) Premarket Notification for VitalSense. Apr. 22, 2004.

MiniMitter Co. Inc. VitalSense Integrated Physiological Monitoring System. Product Description.

MiniMitter Co. Inc. VitalSense Wireless Vital Signs Monitoring. Temperatures.com Mar. 31, 2009.

Mohaverian et al., "Estimation of gastric residence time of the Heidelberg capsule in humans: effect of varying food composition" Gastroenterology (1985) 89:(2): 392-7.

Philips Respironics (http/minimitter.com/products.cfm) Products, Noninvasive Technology to Help Your Studies Succeed. 510(k) Permanent Notification for Vital Sense. Apr. 22, 2004.

Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.

Tatbul et al., "Confidence-based data management for personal area sensor networks" ACM International Conference Proceeding Series (2004) 72.

Xiaoming et al., "A telemedicine system for wireless home healthcare based on bluetooth and the internet" Telemedicine Journal and e-health (2004) 10(S2): S110-6.

Yang et al., "Fast-switching frequency synthesizer with a discriminator-aided phase detector" IEEE Journal of Solid-State Circuits (2000) 35(10): 1445-52.

Yao et al., "Low Power Digital Communication in Implantable Devices Using Volume Conduction of Biological Tissues" Proceedings of the 28th IEEE, EMBS Annual International Conference, Aug. 30-Sep. 3, 2006.

Zimmerman, "Personal Area Networks: Near-field intrabody communication" IBM Systems Journal (1996) 35 (3-4):609-17.

Zworkin, "A Radio Pill" Nature, (1957) 898, 179 Nature Publishing Group.

Arshak et al., A Review and Adaptation of Methods of Object Tracking to Telemetry Capsules IC-Med (2007) vol. 1, No. 1, Issue 1, pp. 35 of 46.

"ASGE Technology Status Evaluation Report: wireless capsule endoscopy" American Soc. For Gastrointestinal Endoscopy (2006) vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; (2003); abstract.

Brock, "Smart Medicine: The Application of Auto-ID Technology to Healthcare" Auto-ID Labs (2002) http://www.autoidlabs.org/uploads/media/MIT-AUTOID-WH-010.pdf.

Delvaux et al., "Capsule endoscopy: Technique and indications" Clinical Gastoenterology (2008) vol. 22, Issue 5, pp. 813-837.

Fawaz et al., "Enhanced Telemetry System using CP-QPSK Band-Pass Modulation Technique Suitable for Smart Pill Medical Application" IFIP IEEE Dubai Conference (N.D.); http://www.asic.fh-offenburg.de/downloads/ePille/IFIP_IEEE_Dubai_Conference.pdf.

Given Imaging, "Agile Patency Brochure" http://www.inclino.no/documents/AgilePatencyBrochure_Global_GMB-0118-01.pdf;(N.D.)4pp.

Gonzalez-Guillaumin et al., "Ingestible capsule for impedance and pH monitoring in the esophagus" IEEE Trans Biomed Eng. (2007) 54(12: 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.

Melanson, "Walkers swallow RFID pills for science" Engadget (2008); http://www.engadget.com/2008/07/29/walkers-swallow-rfid-pills-for-science/.

"New 'smart pill' to track adherence" E-Health-Insider (2010) http://www.e-health-insider.com/news/5910/new_'smart_pill'_monitors_medicines.

"RFID "pill" monitors marchers" RFID News (2008) http://www.rfidnews.org/2008/07/23/rfid-pill-monitors-marchers/.

"SensiVida minimally invasive clinical systems" Investor Presentation Oct. 2009 28pp; http://www.sensividamedtech.com/SensiVidaGeneralOctober09.pdf.

Shrivas et al., "A New Platform for Bioelectronics-Electronic Pill", Cummins College, N.D.; http://www.cumminscollege.org/downloads/electronics_and_telecommunication/Newsletters/Current%20Newsletters.pdf.

"The SmartPill Wireless Motility Capsule" SmartPill, The Measure of GI Health; http://www.smartpillcorp.com/index.cfm?pagepath=Products/The_SmartPill_Capsule&id=17814.

Solanas et al., "RFID Technology for the Health Care Sector" Recent Patents on Electrical Engineering (2008) 1, 22-31.

Swedberg, "University Team Sees Ingestible RFID Tag as a Boon to Clinical Trials" RFID Journal Apr. 27, 2010; http://www.rfidjournal.com/article/view/7560/1.

University of Florida News "Rx for health: Engineers design pill that signals it has been swallowed" (2010) 2pp.; http://news.ufl.edu/2010/03/31/antenna-pill-2/.

ISFET—Ion Sensitive Field-Effect Transistor; MICROSENS S.A. pdf document. pp. 1-4.

Walkey, "MOSFET Struture and Processing"; 97.398* Physical Electronics Lecture 20; pp. 1-24.

"Smartlife awarded patent for knitted transducer" Innovation in Textiles News: http://www.innovationintextiles.com/articles/208.php; 2pp. (2009).

Dhar et al., "Electroless nickel plated contacts on porous silicon" Appl. Phys. Lett. 68 (10) pp. 1392-1393 (1996).

Eldek A., "Design of double dipole antenna with enhanced usable bandwidth for wideband phased array applications" Progress in Electromagnetics Research PIER 59, 1-15 (2006).

Ferguson et al., "Dialectric Constant Studies III Aqueous Gelatin Solutions" J. Chem. Phys. 2, 94 (1934) p. 94-98.

Furse C. M., "Dipole Antennas" J. Webster (ed). Wiley Encyclopedia of Electrical and Electronics Engineering (1999) p. 575-581.

Gaglani S. "Put Your Phone, or Skin, on Vibrate" MedGadget; Mar. 2012 http://medgadget.com/2012/03/put-your-phone-or-skin-on-vibrate.html 8pp.

Halthion Medical Technologies "Providing Ambulatory Medical Devices Which Monitor, Measure and Record" webpage. Online website: http://www.halthion.com/; downloaded May 30, 2012.

(56) References Cited

OTHER PUBLICATIONS

Jimbo et al., "Gastric-fluid-utilized micro battery for micro medical devices" The Sixth International Workshop on Micro and Nanotechnology for Power Geneartion and Energy Conservation Applications, (2006) pp. 97-100.

Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Kamada K., "Electrophoretic deposition assisted by soluble anode" Materials Letters 57 (2003) 2348-2351.

O'Brien et al., "The Production and Characterization of Chemically Reactive Porous Coatings of Zirconium Via Unbalanced Magnetron Sputtering" Surface and Coatings Technology (1996) 86-87; 200-206.

Owano, N., "Study proposes smart sutures with sensors for wounds" PHYS.ORG. Aug. 2012. http://phys.org/news/2012-08-smart-sutures-sensors-wounds.html.

Platt, D., "Modulation and Deviation" AE6EO, Foothills Amateur Radio Society; Oct. 26, 2007; 61 pp.

Rolison et al., "Electrically conductive oxide aerogels: new materials in electrochemistry" J. Mater. Chem. (2001) 1, 963-980.

Roulstone, et al., "Studies on Polymer Latex Films: I. A study of latex film morphology" Polymer International 24 (1991) pp. 87-94.

Shin et al., "A Simple Route to Metal Nanodots and Nanoporous Metal Films"; Nano Letters, vol. 2, No. 9 (2002) pp. 933-936.

U.S. Appl. No. 12/238,345, filed Sep. 25, 2008, Hooman et al., Non-Final Office Action mailed Jun. 13, 2011 22pp.

Winter, J. et al. "The material properties of gelatin gels"; USA Ballistic Research Laboratories, Mar. 1975, p. 1-157.

Hotz "The Really Smart Phone" The Wall Street Journal, What They Know (2011); 6 pp.; http://online.wsj.com/article/SB10001424052748704547604576263261679848814.html?mod=djemTECH_t.

Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.

* cited by examiner

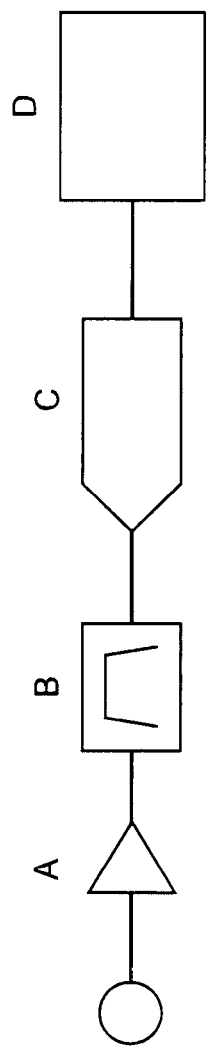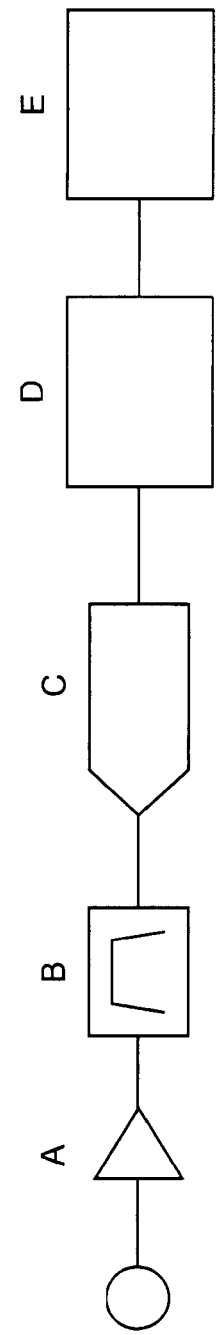
FIG. 6A
FIG. 6B

FIG. 9A

Measured Signals 302 →

|    | C1  | C2  | C3  | C4  | C5  |
|----|-----|-----|-----|-----|-----|
| R1 | .3  | -.9 | .1  | .6  | .3  |
| R2 | -.3 | -.6 | -.2 | -.5 | .1  |
| R3 | .1  | .4  | .8  | .4  | -.6 |
| R4 | .3  | -.5 | .3  | .1  | -.7 |
| R5 | .8  | -.8 | .1  | -.2 | .2  |

← Measured Signal Set 304

FIG. 9B

Transmission Symbols 208 →

|    | C1 | C2 | C3 | C4 | C5 |
|----|----|----|----|----|----|
| R1 | 1  | -1 | 1  | 1  | 1  |

← Transmission Symbol Set 210

FIG. 9C

Hard Code Decision Values 306 →

|    | C1 | C2 | C3 | C4 | C5 |
|----|----|----|----|----|----|
| R1 | 0  | 1  | 0  | 0  | 0  |

← Hard Code Decision Value Set 308

Adjusted Measured Signals 310 →

|    | C1  | C2  | C3  | C4  | C5  |
|----|-----|-----|-----|-----|-----|
| R1 | .25 | -.85| .05 | .55 | .25 |

← Adjusted Measured Signal Set 312

ACTIVE SIGNAL PROCESSING PERSONAL HEALTH SIGNAL RECEIVERS

CROSS-REFERENCE TO RELATED APPLICATIONS

Pursuant to 35 U.S.C. §119 (e), this application claims priority to the filing date of: U.S. Provisional Patent Application Ser. No. 60/866,851 filed Nov. 20, 2006 and U.S. Provisional Patent Application Ser. No. 60/945,251 filed Jun. 20, 2007; the disclosures of which applications are herein incorporated by reference.

INTRODUCTION

Communications play an extremely important role in today's world. Computers, telephones, audio and multimedia players, medical devices, scientific equipment, and other technology both provide and rely on various types of communications.

Communications, however, are susceptible to errors. In particular, noisy transmission environments distort and corrupt communication data. Such environments include the human body, deep space transmissions, high speed transmissions, and high compression storage media. Additionally, devices err in signal generation and measurement related to the communication data.

As such, there is a continued need for improved communication devices and systems. Of particular interest is the development of communications devices and systems that can be employed to reliably communicate information from an in vivo location.

SUMMARY

The invention provides a receiver associated with a body, e.g., located inside or within close proximity to a body, configured to receive and decode a signal from an in vivo transmitter which is located inside the body. Signal receivers of the invention provide for accurate signal decoding of a low-level signal, even in the presence of significant noise, using a small-scale chip, e.g., where the chip consumes very low power. Also provided are systems that include the receivers, as well as methods of using the same.

BRIEF DESCRIPTION OF THE FIGURES

FIGS. 6A to 6C provide circuit diagrams according to certain embodiments of the invention.

FIG. 9A is an illustration of measured signals, according to one embodiment.

FIG. 9B is another illustration of transmission symbols, according to one embodiment.

FIG. 9C is an illustration of hard code decision values, according to one embodiment.

FIG. 9D is an illustration of adjusted measured signals, according to one embodiment.

DETAILED DESCRIPTION

Figure 1:
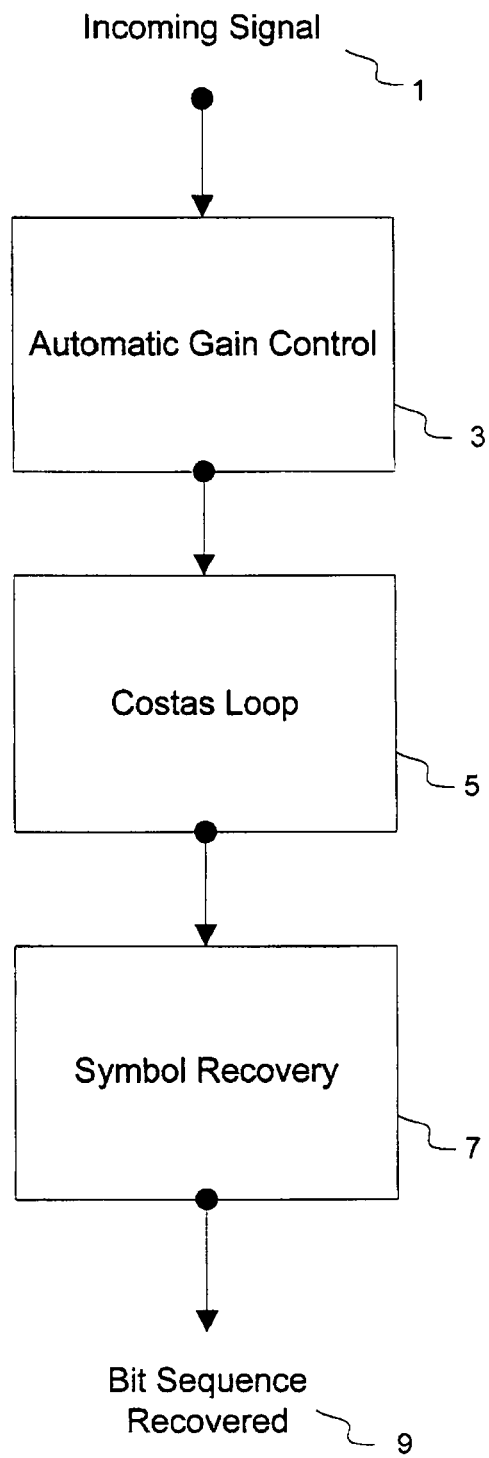
FIG. 1 shows a high-level block diagram of one embodiment of the in-vivo transmission decoder.

The invention provides a receiver associated with a body, e.g., located inside or within close proximity to a body, configured to receive and decode a signal from an in vivo transmitter which is located inside the body. Signal receivers of the invention provide for accurate signal decoding of a low-level signal, even in the presence of significant noise, using a small-scale chip, e.g., where the chip consumes very low power. Also provided are systems that include the receivers, as well as methods of using the same.

In further describing the invention in greater detail, embodiments of the signal receivers are reviewed first in greater detail, followed by a discussion of systems that include the subject signal receivers, methods of using the subject signal receivers and systems and various illustrative applications in which the signal receivers, systems and methods find use. Also reviewed in greater detail below are kits that include the subject signal receivers.

Signal Receivers—Overview

Aspects of the invention include signal receivers configured to receive an encoded signal produced by an in vivo transmitter. Signal receivers of the invention are configured to decode an encoded signal received from an in vivo transmitter. The receivers are configured to decode the encoded signal in a low signal to noise ratio (SNR) environment, e.g., where there may be substantial noise in addition to the signal of interest, e.g., an environment having an SNR of 7.7 dB or less. The receivers are further configured to decode the encoded signal with substantially no error. In certain embodiments, the signal receiver has a high coding gain, e.g., a coding gain ranging from 6 dB to 12 dB, such as a coding gain ranging from 8 dB to 10 dB, including a coding gain of 9 dB. The signal receivers of the invention decode encoded signals with substantially no error, e.g., with 10% error or less.

Signal receivers of embodiments of the invention are configured to receive an encoded signal from a pharma-informatics enabled pharmaceutical composition (e.g., as described in PCT application Serial No. US2006/016370; the disclosure of which is specifically incorporated herein by reference), an ingestible event marker (e.g., as described in provisional application Ser. No. 60/949,223, the disclosure of which is herein incorporated by reference), a smart parenteral device (e.g., as described in PCT/US2007/15547; the disclosure of which is herein incorporated by reference, or analogous device.

In certain embodiments, the receiver is configured to receive a signal conductively from another component, e.g., identifier of a pharmaceutical, a parenteral delivery device, an ingestible event marker, etc., such that the two components use the body of the patient as a communication medium. To employ the body as a conduction medium for the signal, the body of the patient is used as a communication medium. As such, the signal that is transferred between identifier and the receiver travels through the body, and requires the body as the conduction medium.

Mobile embodiments of the signal receiver include ones that are sized to be stably associated with a living subject in a manner that does not substantially impact movement of said living subject. As such, embodiments of the signal receiver have dimensions that, when employed with a subject, such as a human subject, will not cause the subject to experience any difference in its ability to move. As such, in these embodiments, the receiver is dimensioned such that its size does not hinder the ability of the subject to physically move. In certain embodiments, the signal receiver has a small size, where in certain embodiments, the signal receiver occupies a volume of space of about 5 $cm^3$ or less, such as about 3 $cm^3$ or less, including about 1 $cm^3$ or less. In certain embodiments, the signal receiver has a chip size limit ranging from 10 $mm^2$ to 2 $cm^2$.

The signal receivers of interest include both external and implantable signal receivers. In external embodiments, the signal receiver is ex vivo, by which is meant that the receiver is present outside of the body during use.

Where the signal receivers are external, they may be configured in any convenient manner, where in certain embodiments they are configured to be associated with a desirable skin location. As such, in certain embodiments the external signal receivers are configured to be contacted with a topical skin location of a subject. Configurations of interest include, but are not limited to: patches, wrist bands, belts, etc. For instance, a watch or belt worn externally and equipped with suitable receiving electrodes can be used as signal receivers in accordance with one embodiment of the present invention. The signal receivers may provide a further communication path via which collected data can be extracted by a patient or health care practitioner. For instance, an implanted collector may include conventional RF circuitry (operating, e.g., in the 405-MHz medical device band) with which a practitioner can communicate, e.g., using a data retrieval device, such as a wand as is known in the art. Where the signal receiver includes an external component, that component may have output devices for providing, e.g., audio and/or visual feedback; examples include audible alarms, LEDs, display screens, or the like. The external component may also include an interface port via which the component can be connected to a computer for reading out data stored therein. By further example, it could be positioned by a harness that is worn outside the body and has one or more electrodes that attach to the skin at different locations.

In certain external embodiments, the receiver is configured to be in contact with or associated with a patient only temporarily, i.e., transiently, for example while the pill, ingestible marker, etc., is actually being ingested. For example, the receiver may be configured as an external device having two finger electrodes or handgrips. Upon ingestion of a pharma informatics enabled pill, the patient touches the electrodes or grabs the handgrips completely a conductive circuit with the receiver. Upon emission of the signal from the pill, e.g., when the pill dissolves in the stomach, the signal emitted by the identifier of the pill is picked up by the receiver. Where the signal receiver includes an external component, that component may have output devices for providing, e.g., audio and/or visual feedback; examples include audible alarms, LEDs, display screens, or the like. The external component may also include an interface port via which the component can be connected to a computer for reading out data stored therein.

In certain embodiments, the external signal receiver includes miniaturized electronics which are integrated with the electrodes to form a band-aid style patch with electrodes that when applied, contact the skin, and a battery and electronics contained in that package. The bandaid style patch may be configured to be positioned on a desirable target skin site of the subject, e.g., on the chest, back, side of the torso, etc. In these embodiments, the bandaid circuitry may be configured to receive signals from devices inside of the subject, e.g., from an identifier of a pharma-informatics enabled pharmaceutical composition, and then relay this information to an external processing device, e.g., a PDA, smartphone, etc., as described in greater detail elsewhere. Bandaid style devices that may be readily adapted for use in the present systems include, but are not limited to: those described in U.S. Pat. No. 6,315,719 and the like, the disclosures of which are herein incorporated by reference.

In certain embodiments, the signal receiver (i.e., signal detection component) is an implantable component. By implantable is meant that the signal receiver is designed, i.e., configured, for implantation into a subject, e.g., on a semi-permanent or permanent basis. In these embodiments, the signal receiver is in vivo during use. By implantable is meant that the receivers are configured to maintain functionality when present in a physiological environment, including a high salt, high humidity environment found inside of a body, for 2 or more days, such as about 1 week or longer, about 4 weeks or longer, about 6 months or longer, about 1 year or longer, e.g., about 5 years or longer. In certain embodiments, the implantable circuits are configured to maintain functionality when implanted at a physiological site for a period ranging from about 1 to about 80 years or longer, such as from about 5 to about 70 years or longer, and including for a period ranging from about 10 to about 50 years or longer.

For implantable embodiments, the signal receiver may have any convenient shape, including but not limited to: capsule-shaped, disc-shaped, etc. One way we would achieve the small size is by including a rechargeable battery. Because this is not a life-support device, it is a sensing device, it could have a natural life of 2 weeks, and recharge automatically off of coils in the patient's bed so that it would be constantly recharging. The signal receiver may be configured to be placed in a number of different locations, e.g., the abdomen, small of the back, shoulder (e.g., where implantable pulse generators are placed) etc.

In certain implantable embodiments, the signal receiver is a stand alone device, in that it is not physically connected to any other type of implantable device. In yet other embodiments, the signal receiver may be physically coupled to a second implantable device, e.g., a device which serves as a platform for one or more physiological sensors, where the device may be a lead, such as a cardiovascular lead, where in certain of these embodiments the cardiovascular lead includes one or more distinct physiological sensors, e.g., where the lead is a multi-sensor lead (MSL). Implantable devices of interest further include, but are not limited to: implantable pulse generators (e.g., ICDs), neurostimulator devices, implantable loop recorders, etc.

Signal receivers of the invention include a signal receiver element which serves to receive the identifier emitted signal of interest. The signal receiver may include a variety of different types of signal receiver elements, where the nature of the receiver element necessarily varies depending on the nature of the signal produced by the signal generation element. In certain embodiments, the signal receiver may include one or more electrodes for detecting signal emitted by the signal generation element. In certain embodiments, the receiver device will be provided with two electrodes that are dispersed at some distance. This distance allows the electrodes to detect a differential voltage. The distance may vary, and in certain embodiments ranges from about 0.1 to about 5 cm, such as from about 0.5 to about 2.5 cm, e.g., about 1 cm. In certain embodiments, the first electrode is in contact with an electrically conductive body element, e.g., blood, and the second electrode is in contact with an electrically insulative body element relative to said conductive body element, e.g., adipose tissue (fat). In an alternative embodiment, a receiver that utilizes a single electrode is employed. In certain embodiments, the signal detection component may include one or more coils for detecting signal emitted by the signal generation element. In certain embodiments, the signal detection component includes an acoustic detection element for detecting signal emitted by the signal generation element.

A signal receiver may handle received data in various ways. In some embodiments, the signal receiver simply retransmits the data to an external device (e.g., using conventional RF communication). In other embodiments, the signal receiver processes the received data to determine whether to take some action such as operating an effector that is under its control, activating a visible or audible alarm, transmitting a control signal to an effector located elsewhere in the body, or the like. In still other embodiments, the signal receiver stores the received data for subsequent retransmission to an external device or for use in processing of subsequent data (e.g., detecting a change in some parameter over time). The signal receivers may perform any combination of these and/or other operations using received data.

In certain embodiments, the data that is recorded on the data storage element includes at least one of, if not all of, time, date, and an identifier (e.g., global unique serial no.) of each composition administered to a patient, where the identifier may be the common name of the composition or a coded version thereof. The data recorded on the data storage element of the receiver may further include medical record information of the subject with which the receiver is associated, e.g., identifying information, such as but not limited to: name, age, treatment record, etc. In certain embodiments, the data of interest includes hemodynamic measurements. In certain embodiments, the data of interest includes cardiac tissue properties. In certain embodiments, the data of interest includes pressure or volume measurements, temperature, activity, respiration rate, pH, etc.

As summarized above, the signal receivers can be configured to have a very small size. In certain, embodiments, the desired functionality of the signal receiver is achieved with one or more integrated circuits and a battery. Aspects of the invention include receivers that have at least a receiver element, e.g., the form of one or more electrodes (such as two spaced apart electrodes) and a power generation element, e.g., a battery, where the battery may be rechargeable, etc., as mentioned above. As such, in certain embodiments the power generation element is converted to receive power wirelessly from an external location.

Additional elements that may be present in the signal receiver include, but are not limited to: a signal demodulator, e.g., for decoding the signal emitted from the pharma-informatics enabled identifier; a signal transmitter, e.g., for sending a signal from the signal receiver to an external location; a data storage element, e.g., for storing data regarding a received signal, physiological parameter data, medical record data, etc.; a clock element, e.g., for associating a specific time with an event, such as receipt of a signal; a pre-amplifier; a microprocessor, e.g., for coordinating one or more of the different functionalities of the signal receiver.

Aspects of implantable versions of the signal receiver will have a biologically compatible enclosure, two or more sense electrodes, a power source, which could either be a primary cell or rechargeable battery, or one that is powered by broadcast inductively to a coil. The signal receiver may also have circuitry consisting of: a demodulator to decode the transmitted signal, some storage to record events, a clock, and a way to transmit outside the body. The clock and transmit functionality may, in certain embodiments, be omitted. The transmitter could be an RF link or conductive link to move information from local data storage to an external data storage.

For the external signal receivers, embodiments include structures that have electrodes opposed to the skin, the demodulator, storage, and power. The communication may be wireless or performed over one or more conductive media, e.g., wires, optical fibers, etc.

In certain embodiments, the same electrodes are used for receiving and transmitting signals. One mode might be to have for example a wristwatch which is conductively in contact with the body, where to move the data from the implant to the wristwatch one would send currents out the pads and those would be received by the wristwatch. There are a number of RF techniques for getting the transmission out of the body that may be employed, such as inductive protocols that employ coils. Alternatively, one could employ electric fields, where one would use insulated electrodes, not conductively contacted electrodes.

In certain embodiments, the components or functional blocks of the present receivers are present on integrated circuits, where the integrated circuits include a number of distinct functional blocks, i.e., modules. Within a given receiver, at least some of, e.g., two or more, up to an including all of, the functional blocks may be present in a single integrated circuit in the receiver. By single integrated circuit is meant a single circuit structure that includes all of the different functional blocks. As such, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain embodiments of the present invention may be hybrid integrated circuits, which are miniaturized electronic circuits constructed of individual semiconductor devices, as well as passive components, bonded to a substrate or circuit board.

As reviewed above, the signal receivers exhibit reliable decoding of an encoded signal even in the presence of substantial noise and a low SNR. This functional aspect of the receivers of the invention is provided by one or more of: Coherent demodulation, e.g., Costas loop demodulation, accurate low overhead iterative decoding, Forward Error correction and Noise Cancellation.

Demodulator

In one embodiment, the binary code is modulated to the carrier signal using binary phase shift keying (BPSK). In standard BPSK the carrier signal is modulated by shifting its phase by 0° for a binary "0" and 180° for a binary "1." Note that this is an arbitrary assignment, and a phase shift of 0° may instead correspond to a binary "1", with a phase shift of 180° corresponding to a binary "0." This allows a lower signal to noise ratio (SNR) than frequency shift keying or amplitude shift keying, allowing the binary code to be accurately decoded in the presence of a greater amount of noise. This is useful in many environments where there are many sources of noise in the same frequency spectrum, such as in a hospital.

The in-vivo transmission decoder can successfully decode an incoming BPSK signal with negligible error with an SNR as low as about 3 dB, more specifically about 6 dB, most specifically about 7.7 dB. The signal can be decoded with about 10% error in the decoded bits with an SNR as low as about 0 dB, more specifically about 3 dB, most specifically about 4.7 dB. The actual minimal SNR needed depends on the amount of error that is allowable. With higher allowable error, the signal can be successfully decoded with a lower SNR. With error checking algorithms, some error may be acceptable, and the SNR could be even lower, while still successfully decoding the signal.

Because the original data bit signal may be a square wave which contains some high frequency components, the modulated signal may have some high frequency components as well. These can corrupt the signal depending on the sampling rate. To alleviate this, an anti-aliasing filter can be included in some embodiments. The anti-aliasing filter can filter out the high frequency components and clean up the analog signal before sampling. Typically, a low-pass filter with a cutoff of one half of the sampling frequency is used.

In one embodiment of the inventive in-vivo transmission decoder, the receiver can have an analog to digital converter to sample the input signal. The sampling rate can be varied according to the frequency of the incoming signal, noise level, or other factors.

In one embodiment of the in-vivo transmission decoder, the sampling rate can be actively adjusted according to measured factors such as SNR. When more noise is present, a higher sampling rate can be used, so that the signal can still be decoded accurately. However, when the SNR is higher, the sampling rate can be lowered without affecting the accuracy of the recovered signal. The in-vivo transmission decoder can compare the measured SNR to a threshold, and use the ratio to adjust the sampling rate. There can be a lower limit past which the sampling rate won't be lowered.

In laboratory tests conducted by some of the present inventors, the signal was successfully decoded in the presence of noise with a sampling rate as low as four times the frequency of the incoming signal. The in-vivo transmission decoder can accurately decode the received signal with a sampling rate as low as about 2 times the frequency of the received signal, more specifically about 3 times the frequency of the incoming signal, most specifically about 4 times the frequency of the incoming signal. By actively adjusting the sampling rate to be as low as necessary, the power used by the receiver can be conserved.

In one embodiment of the in-vivo transmission decoder, there is an automatic gain control (AGC) block, which actively adjusts the gain to maximize the effectiveness of the Costas loop. The AGC block can also find the strongest frequency of the received signal, and tune other components to adjust for that. This allows the receiver to actively adjust to variations in frequency and power of the incoming signal, as well as drift of the signal over time.

In one embodiment, the AGC block includes a Fast Fourier Transform (FFT) calculation, which is used to find the power spectrum and strong frequency of the incoming signal. Because the AGC block needs a group of points to calculate the FFT, a buffer can be used. The buffer can be set to collect a certain number of points before sending them on to the FFT for processing. The size of the buffer used can vary depending on characteristics of the incoming signal, such as signal uniformity and cycle length. The buffer size should be small enough to provide fast processing and adjustment to changes in the signal, but large enough that the FFT results do not vary widely with instantaneous changes in the signal.

Once the signal is buffered, the signal can be passed to the FFT function. This portion computes the FFT of the input signal, giving the power spectrum. The block then locates the frequency that has the highest amplitude in the FFT signal, $f_{max}$. The FFT calculation requires a finite number of samples from the incoming signal in order to produce accurate results, which is why the buffer is used. The frequency information is passed on to subsequent blocks and can be used to tune various components, such as the band-pass filters and voltage controlled oscillators of a Costas loop.

The AGC block also amplifies the signal, adjusting the gain to achieve a predetermined signal power. The strength of the received signal will vary depending on many factors, such as location and orientation of the transmitter. To adjust for this, the AGC block finds the amplitude of the strongest frequency component in the power spectrum. This amplitude value is divided into a normalized power value which gives the proper gain to apply to achieve that signal strength. The original digital signal which was input into the ACG block is then amplified by the calculated gain and passed on.

The amplified digital signal can then be passed through a band-pass filter before entering the Costas loop. The band-pass filter can be tuned to have a center frequency equal to $f_{max}$, the strongest frequency component found in the AGC block. This is included to clean up the signal further and eliminate noise components at frequencies that are not part of the transmitted signal. Although the transmitter is designed to output the data signal at a set carrier frequency, the actual output of each unit may vary. By actively tuning the center frequency to $f_{max}$, the band-pass filter can adapt to variations in the frequency sent out by the transmitter, and to frequency drift of the signal over time. The bandwidth of the band-pass filter can be set to a percentage of the strongest frequency of the incoming signal. Alternatively, the bandwidth can be set to a specific value.

In some embodiments, there can be a first-in first-out block included before the FFT in the AGC block. This can be implemented in cases where the processing time of subsequent blocks is longer than the rate of the data coming in. The signal is then sent into a Costas loop for demodulation of the signal. The Costas loop reconstructs a replica of the carrier which is locked in frequency and phase to the incoming carrier, so the phase of the received signal can be extracted, giving an approximation of the original binary signal.

The Costas loop employed can be very similar to those known in the art, with the exception that the voltage-controlled oscillator is tuned to $f_{max}$. This allows the Costas loop to adapt to changes in the transmitted carrier frequency and lock on to the correct signal. In lab tests conducted by some of the present inventors, the receiver was able to adjust to an instantaneous change of up to about +/−10 kHz, when originally configured to receive a 100 kHz signal.

The in-vivo transmission decoder can track an instantaneous change in frequency of up to about 25% of the signal frequency, more specifically up to about 25% of the signal frequency, most specifically up to about 10% of the incoming signal. Depending on the size of the frequency change, the receiver can typically lock onto the new frequency within a few cycles of the waveform.

In another embodiment, there can be an integrator added to the Costas Loop between the multiplier and the low-pass filter in the VCO branch. This helps to smooth out the signal more than the low-pass filter alone. In another embodiment, there can be a low-pass filter added to the output of the Costas loop to clean up the signal before the signal recovery block.

The Costas loop can also output the detected power of the signal. In some embodiments, this can be used to tune the gain in the AGC block. This can be used in addition to or instead of the other gain adjustments.

After the signal goes through the Costas loop, the signal clock must be extracted in order to determine when each bit begins and ends. One way of accomplishing this is through the use of an Early-Late Gate. The Early-Late Gate is a phase locked loop with two integrators which each maintain a running sum of half of the symbol period, T, of the incoming data. The early gate sums the data during the first half of the symbol period, or from time t−T/2 to t. The late gate sums the signal during the second half of the symbol period, or from time t to t+T/2. The late gate is then subtracted from the early gate, and this difference is outputted. This output will be zero as long as a string of 0's or 1's is received. When there is a transition from a 1 to a 0, or from a 0 to a 1, the early late-gate output becomes non-zero. The next time, t, that the output becomes zero will be the center of the corresponding symbol.

In order to compensate for different sampling rates and signal frequencies, the number of samples to use for the early and late gates is actively computed instead of using a standard value. With a signal which is set to broadcast each bit for 16 cycles of a sine wave, the number of sampled points in half of the symbol period will be the time needed for 8 periods of the sine wave divided by the time between samples. Or, put in different terms:

$$T_g = 8f_s/f_c$$

Where $T_g$ is the time of the early gate and late gate, $f_s$ is the sampling frequency and $f_c$ is the frequency of the transmitted signal. Frequency fc can be found by using the frequency that the VCO locks onto in the Costas loop.

When a known preamble or start sequence is sent, the time that a specific bit occurs can be determined. As an example, assume a preamble of a sequence of 16 zeros is followed by a known start sequence of 0010, which is then followed by an 8 bit ID sequence and a 4 bit sleep period where no signal is sent. The algorithm can first identify where the sequence of zeros occurs by looking for a period of no change in the signal. This prevents the timing problems that would occur if the receiver begins picking up the signal in the middle of a data packet. Since the period of zeros is longer than any other possible sequence of no changes, the algorithm can correctly identify where this preamble occurs. Once the preamble is identified, the algorithm can begin looking for the start sequence. During the first two zeros of the example start sequence, the early-late gate output will remain zero. The first non-zero value will occur at the transition from 0 to 1. The early-late gate will then cross zero again at time=$t_3$, the center of the 1 bit in the signal. Since the symbol period, T, is known, once the time at which the third bit of the start bit sequence occurs is known, the time for all other symbols can be determined. In this example, the $n^{th}$ symbol will occur at $t_n = t_3 + (n-3)T$.

In practice, the early-late gate output may not be exactly zero during non-transition periods, but will instead hover around zero due to noise. In order to mark the non-zero point, a threshold is set which is above the level of noise, but below the amplitude of a bit. The receiver can compare the early-late gate output against this threshold, and set a flag when it is crossed. Once the threshold is crossed, the receiver then looks for a zero-crossing in the signal.

There is a 180° phase ambiguity which is inherent in any Costas loop implementation, meaning the Costas loop is just as likely to lock in to the phase of a "0" as it is a "1". There are several ways to deal with this which are well known in the art.

In one embodiment, once the symbol timing is recovered, the known start sequence can be looked at in the Costas loop output. Two threshold values can be used, one positive and one negative. When the positive threshold is passed, the index of the digital signal can be stored, and compared against the index stored for the negative threshold to determine which threshold was passed first. In the case of the known start bit 0010, if the positive threshold is passed first, that would indicate that a larger Costas loop output represents a "0," while a smaller output represents a "1." If the negative threshold is passed first, that would indicate that a larger Costas output represents a "1," while a smaller output represents a "0." At this stage, the bit sequence can be accurately extracted, and the ID of the transmitter can be identified.

Other techniques for symbol timing recovery that can be utilized include differential decoding, Gardner timing recovery, squaring timing recovery, and Mueller-Mueller timing recovery.

The data from the transmitter can be repeated at regular intervals. This reduces error and allows the receiver many opportunities to decode the signal. Once the symbol recovery algorithm identifies the start bit sequence and begins reading the bits, a delay can be used to restart the symbol recovery algorithm for the next data packet. Because of the Costas loop ambiguity, the symbol timing recovery algorithm will need to be restarted for each data packet. Because the ID will be a known number of bits, a predetermined delay can be applied.

FIG. 1 shows a high-level flow chart of one embodiment of the receiver algorithm. The input signal 1 is picked up by an antenna and fed into AGC block 3. The AGC block 3 samples the signal, finds the strong frequency, and amplifies the signal to a normalized power. The Costas loop block 5 then demodulates the incoming digital signal. Symbol recovery block 7 is used for symbol timing recovery of the Costas loop output. After the symbol recovery block 7, the signal has been demodulated and the timing has been recovered, and the bit sequence 9 is extracted.

For the purposes of demonstrating the inventive algorithm, a sample data signal will be used. The data signal used for this example is a 32 bit signal. The first 16 bits are known to be all zero. The zero period is followed by a start preamble which is 0010. After the preamble is the 8-bit ID sequence. The remaining 4 bits are a quiet period. In this example, the binary signal is modulated using BPSK to a carrier signal which transmits at a nominal frequency of 100 kHz. Each bit is 16 periods of the sine wave long, meaning for each bit the sine wave will be in the corresponding phase for 16 periods. This corresponds to an overall time for each 32 bit signal of about 5.12 ms. It is understood that this sample data signal is only an example, and the receiver algorithm can be applied to any BPSK signal. Also, one of the key aspects of the inventive algorithm is that it can account for variations in the actual carrier frequency of the transmitted signal, so the transmitted signal need not be extremely precise between different transmitters.

The algorithms discussed below were created using Simulink as a tool. The algorithms can then be transferred to hardware using known techniques. One such technique is to use Mathworks Real-Time Workshop to convert the Simulink developed algorithm into C code. Then Texas Instruments Code Composer Studio, or other similar development tool, can be used to convert the C code into assembly language. The assembly language can be programmed onto a digital signal processing (DSP) chip, such as Texas Instruments model TMS320VC5509 or a similar chip.

Figure 2:
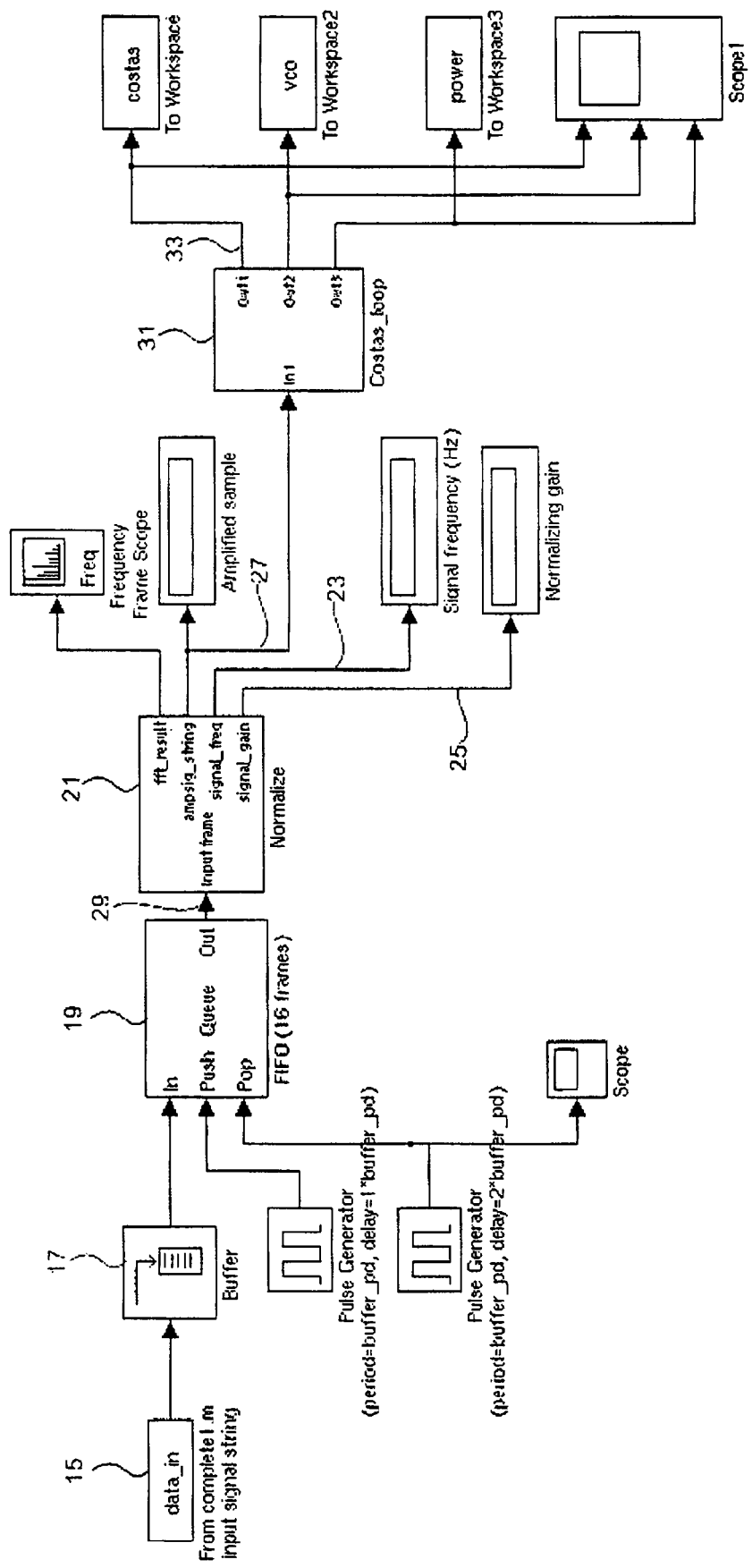
FIG. 2 shows a block diagram of one embodiment of the automatic gain control and Costas loop blocks of the in-vivo transmission decoder.

FIG. 2 shows a block diagram created in Simulink that shows one embodiment of the AGC block and Costas loop from FIG. 1. Incoming data 15 is actual data received in an animal study, sampled at 2 MHz. The animal study used a PCB inserted in the stomach of a pig to transmit the data signal. The signal was received by subcutaneous titanium electrodes and skin patches. This data was sampled at 2 MHz and fed into the software at data block 15. Since this is actual data which was collected in-vivo, it is a demonstration of the effectiveness of the algorithm in an in-vivo setting. The data 15 fed into buffer 17, which is set to collect $2^{15}$ points. With a sampling rate of 2 MHz and a data period of about 5.12 ms, this means the buffer collects a little over 3 packets of data. This can be adjusted depending on various factors such as signal characteristics and noise level. Using more packets of data gives a more stable FFT that will not change as much in successive iterations. Since the output of the FFT block will be used to tune the gain and center frequency of other components, these variables will not have to be adjusted as much and will not vary as widely as if a smaller set of data is used for the FFT.

The buffered output is then sent to a first-in first-out (FIFO) block 19 which manages the data to ensure that it is processed in order and will store it until the subsequent blocks are ready for it. This may be necessary because the FFT block, Costas loop, and Early-Late Gate can take time to complete.

The data is then sent to a FFT block 21, which calculates the fast Fourier transform of the amount of incoming data determined by the buffer 17. The FFT block finds the strongest frequency by finding the frequency which gives the maximum value in the FFT. This frequency is output as a variable 25, labeled "signal_freq", which can be used by other blocks.

The Costas loop works best when the power of the incoming signal is normalized. This is done in the FFT block also. The amplitude of the power spectrum given by the FFT at the frequency "signal_freq" is found and compared to a constant value which represents the desired power for the Costas loop. This gives the gain 25 which is necessary to achieve that signal power, and this gain is applied. The FFT block 21 then outputs signal 27 which is the incoming signal 29 amplified by the calculated gain 25.

This amplified signal is fed into the Costas loop 31. The Costas loop demodulates the BPSK signal. The Costas loop used is similar to those which are well known in the art, except that the components can be actively tuned according to measured characteristics of the incoming signal. The Costas loop will be discussed in greater detail below. The Costas loop output 33 is sent to a matlab workspace where the final symbol decoding is done, including an Early-Late Gate.

Figure 3:
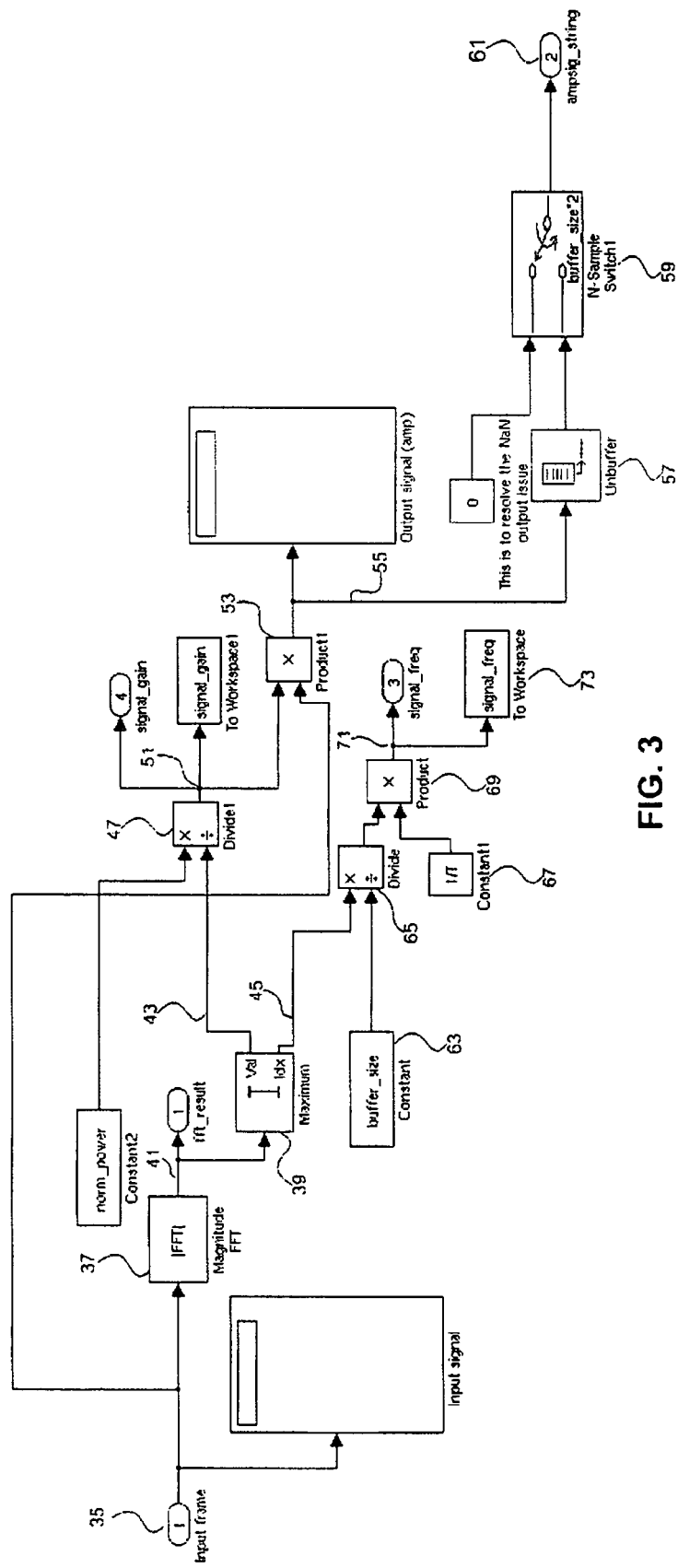
FIG. 3 shows a block diagram of one embodiment of the automatic gain control block of the in-vivo transmission decoder.

FIG. 3 shows a more detailed block diagram of FFT block 21 from FIG. 2. The output from the FIFO enters FFT block 21 at input 35. Magnitude FFT block 37 performs a fast Fourier Transform, which gives the power spectrum of the signal as a function of frequency. Maximum block 39 finds the point in FFT 41 where the amplitude is at a maximum, and outputs the value 43 and index 45 of where that point occurs in the data string. The maximum value 43 is fed into divider block 47. Divider block 47 takes the normalized power constant 49, which is a predetermined value of the desired signal power, and divides it by maximum power value 43, which yields signal gain 51. Signal gain 51 is then applied to input 35 in multiplier block 53 in order to achieve a signal with a normalized power for the Costas loop. Before being sent to the Costas loop, the amplified signal 55 is unbuffered by unbuffer block 57 in order to convert the signal back to a steady stream. Switch 59 is there to deal with a problem with dividing by zero in the software, but is not necessary for the algorithm. The output of the FFT block is the amplified, unbuffered signal 61.

The FFT block in FIG. 3 also finds and outputs the frequency at which the maximum amplitude of the power spectrum of the signal occurs. Maximum block 39 outputs index 45 which is the index of the data point in the digital FFT string. The index 45 of the maximum point is divided by the buffer size 63 in divider block 65. This gives the relative position of the maximum point in the range of 0 to the maximum frequency of the spectrum. Constant 67 is one divided by the sampling time, which will give the maximum frequency of the spectrum. The fractional value 69 found in divider block 65 is then multiplied by frequency spectrum constant 67 to yield the absolute frequency value 71 of the maximum power in the signal. This is set as a constant 73 which can be used in other blocks to tune components such as filters and voltage controlled oscillators.

Figure 4:
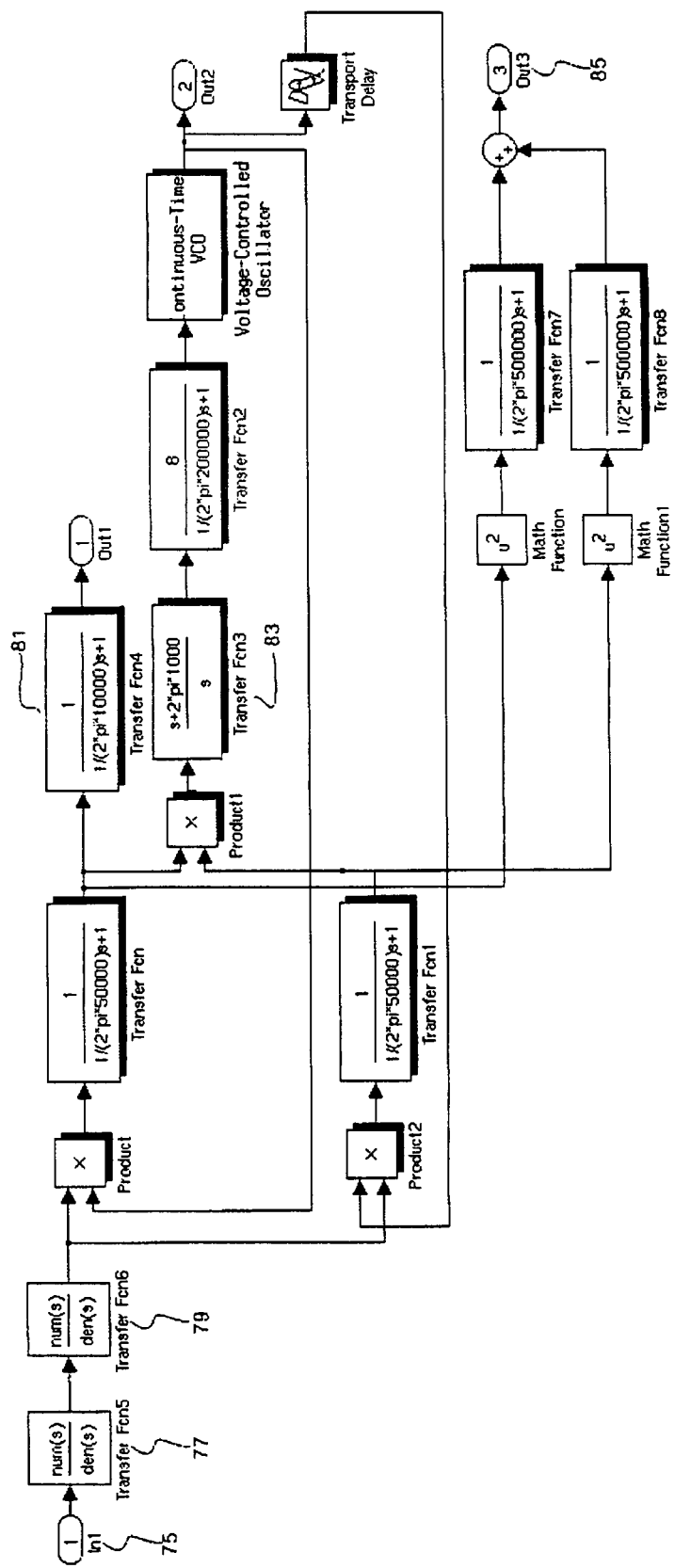
FIG. 4 shows a block diagram of one embodiment of the Costas loop block of the in-vivo transmission decoder.

FIG. 4 shows a more detailed block diagram of Costas loop 31 from FIG. 2. The amplified, unbuffered output from the FFT block enters the Costas loop at input 75. It is band-pass filtered by transfer functions 77 and 79. The use of two filters gives a sharper roll-off than if one filter were used. The transfer functions of filters 77 and 79 are defined using variables in Simulink. The center frequency of band-pass filters 77 and 79 is set to be the "signal_freq" variable 73 from the FFT block in FIG. 3. The bandwidth of the band-pass filters 77 and 79 are set to be one eighth the center frequency.

By actively adjusting the center frequency of the filters at the input of the Costas loop, the receiver can adjust to changes in the transmit frequency while maintaining a relatively narrow band. This allows the transmitter-receiver system to be used under varying conditions, such as supply voltage and temperature, which may alter the transmitted frequency. This is especially useful when the signal is to be transmitted and received in a poor signaling environment such as the body, and areas where a lot of signal noise is present, such as in hospitals.

The rest of the Costas loop is standard and well-known in the art, with the exception of added low pass filter 81, integrator 83, and power output 85. The added low-pass filter 81 and integrator 83 are included to further clean up the signal, but are not necessary for the Costas loop to work. Power output 85 is included in Simulink in order to measure the signal-to-noise ratio (SNR), but does not play a part in the signal analysis in the current embodiment. In other embodiments, the power output 85 can be used to tune other components. For example, the power output 85 can be linked back to the gain stage 53 of the FFT block in FIG. 3. The output of the Costas loop is essentially a filtered version of the original binary code, except that the polarity can be reversed depending on whether the Costas loop locked onto a "0" or a "1."

Figure 5:
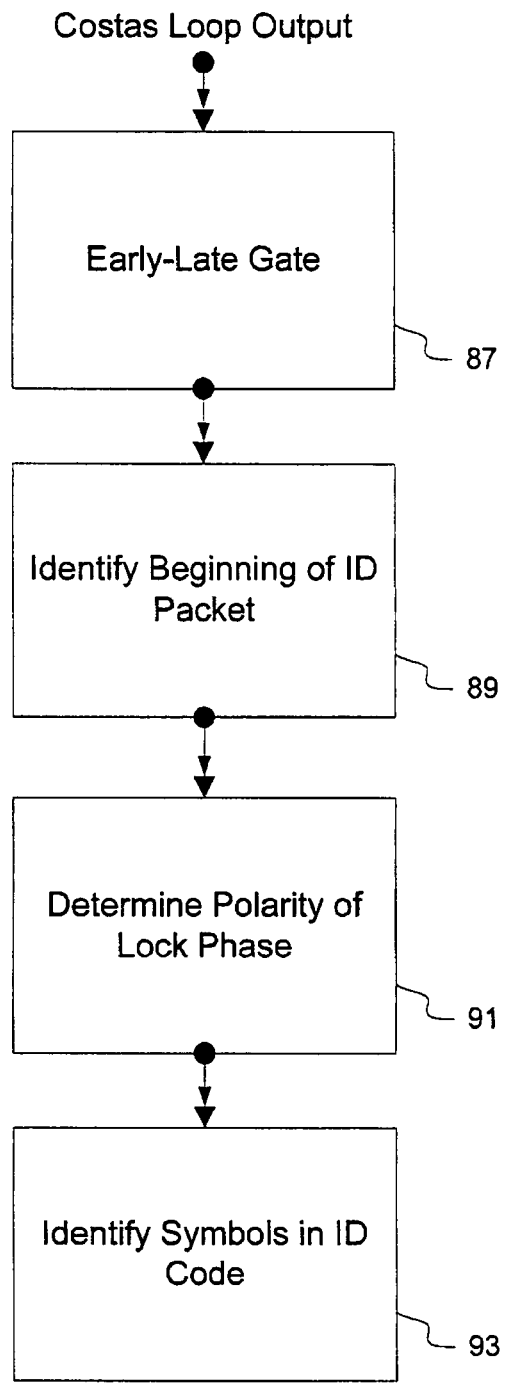
FIG. 5 shows a block diagram of one embodiment of the symbol recovery block of the in-vivo transmission decoder.

FIG. 5 shows an embodiment of the symbol recovery block 13 from FIG. 1. In this embodiment, the symbol recovery block takes the output of the Costas loop and performs an early-late gate calculation 87. The early-late gate results are used to identify the beginning of the ID sequence in block 89. This block extracts the timing of the signal to identify the indices at which the center of each bit occurs, and also identifies the start bit in order to locate where the ID code starts. From this information, the index of the Costas loop output which represents the phase of each bit can be found. Block 91 determines the polarity of the lock phase in the Costas loop. This finds whether the Costas loop locked into the phase of a binary "1" or "0," and sets decision points for each bit. Next, block 93 looks at the Costas loop output signal at each ID index that was found in block 89 and decides whether each is a "1" or a "0." At that point, the 8-bit ID has been successfully extracted.

In certain embodiments, the architecture is, configured in view of the need to demodulate/decode where the uncertainty in the carrier frequency is +/−20%, where a Costas loop (e.g., as described above) might be able to lock onto a signal where the carrier uncertainty is +/−6%, and where coherent detection requires a carrier uncertainty of <1%. In certain embodiments, overall packaged circuit size is important to achieve a device that is comfortably usable. In addition, power consumption is also important for battery longevity in certain embodiments.

FIG. 6A illustrates an architecture employed in certain embodiments. As shown in FIG. 6A, the structure gains up the signal (A), applies an anti-aliasing filter (B), digitizes the signal using an ADC (C), and then identifies the carrier, demodulates and decodes using DSP techniques coded into a general purpose DSP or microcontroller (D). The anti-aliasing filter is designed in consideration of the range of carrier frequencies and the sampling rate of the ADC. The sampling rate of the ADC is in certain embodiments at least >3× the highest possible carrier frequency, such as 4× the highest possible carrier frequency. The resolution is selected based upon the dynamic range of the signal.

In the alternative configuration illustrated in FIG. 6B, the carrier identification, demodulation, and decode functions are performed by, a combination of ASIC/FPGA/Co-Processor (D) and low power microcontroller/processor (E). The ASIC/FPGA/Co-Processor implement the math intensive functions that are part of the carrier identification, demodulation, and decoding. These functions may include FFT, filters, decimation, multiplication, etc.

Figure 6C:
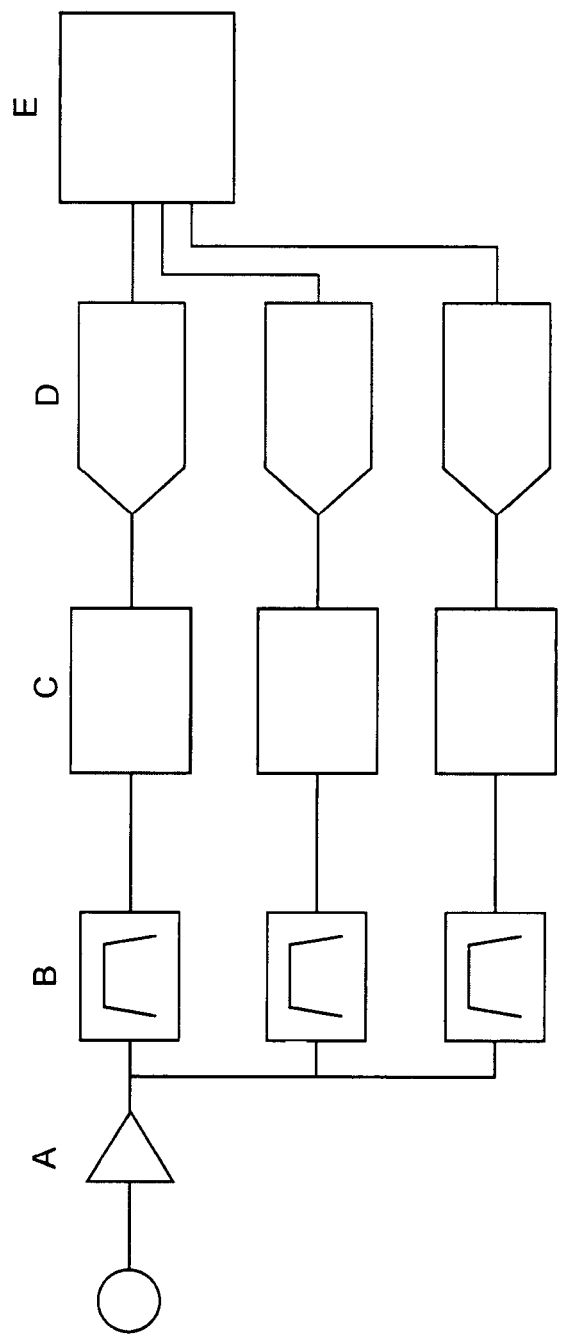

FIG. 6C illustrates an architecture according to an embodiment that implements much of the signal processing using analog circuit techniques. Block (A) still gains up the received signal. Block (B) implements a band-pass filter. In embodiments of these circuits, the bandwidth is set at f/8 where f is the anticipated carrier frequency. Block (C) implements a demodulation function. Block (D) is an ADC. The sampling rate determined by the maximum symbol rate*4. Decoding is performed in a DSP or microprocessor (E), but its performance requirements are much relaxed compared to that in FIG. 6A. Blocks (B), (C), and (D) are duplicated with separate distinct bandwidths to the range of carriers. Alternatively, the decode function may be implemented using analog circuitry, further reducing the specifications on block (E).

Each figure contemplates using discrete components to implement the circuitry. However 2 or more blocks in any figure may be implemented in an ASIC, thereby reducing the component count and therefore the overall size. While FIG. 6C may have a larger component count (and size) if implemented discretely, it could also be implemented as an ASIC. Any one of the circuits illustrated in FIGS. 6A to 6C could be implemented in a single chip (system on chip—SOC). In certain embodiments, the only limitation may be that the input referred noise on block (A) limits the overall performance of the system. Minimum noise requires a bi-polar transistor input stage which is not possible on standard digital IC processes, but found in many "mixed-signal" processes.

Coherent Demodulation

The demodulation of BPSK in the presence of AWGN (Additive White Gaussian Noise) is performed in certain embodiments to minimize BER (Bit Error Rate) using coherent demodulation.

In these embodiments, the in vivo transmitter facilitates the receiver coherent demodulation process by sending a pilot carrier in the "front porch" of each burst of BPSK modulation. This protocol provides a stable carrier at full amplitude and a reference phase that corresponds with the transmission of a 0 bit. The presence of a front porch gives a useful detection signature to the receiver and a large number of carrier cycles for accurate estimation of the carrier frequency and phase.

An additional practical use is made of the carrier frequency to simplify derivation of the data rate. The transmitted signal is formatted to have the data clock frequency an integer division of the carrier frequency. This permits easy and rapid data clock acquisition once the carrier acquisition has been accomplished.

The receiver samples the incoming signal at a rate of around 4 times the carrier frequency in certain embodiments. This signal is mixed with a DDS (Direct Digital Synthesizer) set to the nominal carrier frequency to create complex baseband (real and imaginary components). The output of the mixer is low pass filtered and decimated. The low pass filter bandwidth must be sufficiently wide to capture frequencies in the band due to carrier oscillator uncertainty and frequency hopping dither. The frequency of the BPSK is subsequently in the vicinity of 0 Hz with a frequency accuracy of +/−20%.

The receiver squares the complex baseband BPSK signal to create a strong double frequency line. The front porch signal and following BPSK modulation all contribute to this line. The squared complex time domain signal is transformed to the frequency domain using an FFT (Fast Fourier Transform). The peak energy bin is identified as the 2× carrier frequency. This frequency is divided by two to provide an estimate of the carrier offset frequency to about 0.1% accuracy using a 1024 point FFT.

The complex baseband signal is then mixed a second time with the determined offset frequency. The result after narrow band low pass filtering is a complex BPSK signal centered at 0 Hz with an accuracy of 0.1%. The bandwidth of the narrow band low pass filter corresponds with the half bandwidth of the BPSK signal.

The front porch signal is then extracted. The frequency offset is determined by first computing the phase (phi=arctan (imag/real)) of all sample points in the front porch, and then estimating the slope of phi vs. time using a least mean square fit to a line. The slope of the line corresponds to the residual frequency offset. The complex baseband signal is then mixed a third time to remove this frequency offset with an accuracy better than 0.01%.

The complex signal front porch is then averaged to determine the mean imaginary and real values. The arctan(mean imag/mean real) provides the front porch phase. A rotator factor is computed based on this phase to rotate the BPSK on to the imaginary axis with the front porch at 270 degrees.

A second averaging is then performed on the entire rotated BPSK signal to identify the center of gravity of the 90 degree (data=1) and the BPSK is rotated in a similar manner to center this on the imaginary axis. The imaginary signal is then sliced to extract the data.

The sliced data is strobed with a data clock that is derived from the prior determination of the carrier frequency and apriori knowledge of the integer factor relating the carrier frequency to the data clock frequency.

In embodiments of the above protocols, it is assumed that the carrier frequency holds to a sufficient accuracy in frequency and phase through the duration of the entire burst. In the event that this is not the case, adaptive frequency tracking can be implemented using a decision directed carrier recovery phase locked loop such, as the Costas loop as described above. The Costas loop operates by driving a rotator to maintain zero average error in phase of the baseband signal.

Accurate, Low Overhead Iterative Decoding

In certain embodiments, the receivers include an accurate, low overhead interative decoder, also referred to herein as a communications decoder. The communications decoder provides, for the first time, highly accurate communications in a simple, elegant, and cost-effective manner despite the presence of significant signal distortion due to noise and other factors. The communications decoder utilizes error correcting codes and a simple, iterative process to achieve the decoding results. The communications decoder can be used across multiple and varied applications to realize a low cost, high coding gain.

Broadly, an embodiment of a communications decoder provides decoding capabilities for data communications. An embodiment of a communications decoder provides a high coding gain with minimal overhead. In some instances, the communications decoder facilitates data transmission rates close to the theoretical maximum, the Shannon Limit, while minimizing processing overhead. The low overhead ensures cost-effective implementations. Various implementations of the present invention include hardware, software, and circuitry.

Further, the communications decoder is applicable to any communications environment, particularly noisy communications environments, and not just to receivers of signals transmitted from in vivo transmitters. For example, the communications environments include inter-body and intra-body communications; deep space transmissions; optical communications; radio communications; storage media; multimedia devices; and wireless communications. Multimedia devices include, for example, audio and multimedia receivers associated telephones, stereos, audio players, and multimedia players. Deep space transmissions include satellite communication devices. Wireless communications include wireless devices such as wireless headsets; audio and multimedia devices and equipment, such as audio players and multimedia players; telephones, including mobile and cordless telephones; and computers and computer-related devices and components, such as printers.

However, for ease of description, the communications decoder will be described further primarily in terms of embodiments in which it is present in a receiver of an in vivo transmitted signal.

Inter-body and intra-body communications include, for example, software, circuitry, and devices associated with data reception from implantable, ingestible, insertable, and attachable medical devices associated with the human body or other living organisms. The medical devices comprise, integrate, or are otherwise associated with the communications decoder. One example is a receiver such as is described in PCT/US2006/16370 titled "Pharma-Informatics System" and filed on Apr. 28, 2006; as well as U.S. Provisional Application Ser. No. 60/887,780 titled "Signal Receivers for Pharma-Informatics Systems" filed on Feb. 1, 2007 and U.S. Provisional Application Ser. No. 60/956,694 titled "Personal Health Signal Receivers" filed on Aug. 18, 2007. Each of the foregoing applications is hereby incorporated by reference in its entirety.

More particularly, communication between devices can be accomplished using various techniques. At origin, for example, an encoder device converts (modulates) data formatted as binary digits (bits) to transmission symbols associated with analog signals. A transmitter transmits the data to a receiver. At destination, a receiver measures each analog signal of the analog signals. Based on the measurement, a decoder converts (demodulates) each analog signal to a bit and assembles the converted bits into data. Some or all of the data, however, may be in error. One common error occurs in noisy communications environments when the noise changes the signal to a measurement that, when demodulated, results in a bit that does not coincide with the original bit transmitted at origin.

Using certain current error detection techniques, the presence of errors in data can be detected. Current error detection techniques include the use of error correcting codes such as turbo codes and low-density parity-check (LDPC) codes.

Under existing turbo codes methods, the transmitter or encoder generates three variations, or sub-blocks, of the data: the original data, an encoded version of the original data, and an encoded version of the permutated data. Each of the sub-blocks is transmitted. The receiver converts the signals of the three sub-blocks into "most likely" data and compares the three sets of estimated data. A decision is taken from the comparison to arrive at a final "most likely" decision for the decoded data. Such a method is complex and costly.

Under existing LDPC code methods, the transmitter or other device encodes the original data (bits) with one or more error correcting codes (hereinafter, "codes"), as discussed in an article entitled "Low Power Digital Communication in Implantable Devices Using Volume Conduction of Biological Tissues", which is incorporated here in its entirety. (Heung-No Lee, R. J. Sclabassi, Mingui Sun, and Ning Yao, "Low Power Digital Communication in Implantable Devices Using Volume Conduction of Biological Tissues", Proceedings of the $28^{th}$ IEEE EMBD Annual International Conference New York City, USA, Aug. 30-Sep. 3, 2006, pp. 6249-6252.) The codes include parity codes, Hamming codes, and Golay codes. The transmitter converts the bit set to analog signals, e.g., transmission symbols, and transmits the transmission symbols. The receiver decodes the analog signals to the "most likely" bit. Put another way, the receiver rounds the measurement of the transmitted signal to the nearest bit.

The rounding of the measurement to the nearest bit, however, does not always result in correct data. In particular, noise can corrupt the signal. This can result in a signal measurement that, when rounded to the nearest bit, does not correspond to the original bit converted and transmitted at origin.

To ascertain if such errors have occurred, an error check of the bits can be performed using the codes. Existing parity code methods employ the use of a parity code to check for parity errors at destination. The presence of a parity error suggests one or more occurrences of error in a bit set, i.e., one or more converted bits at destination do not match the corresponding bit generated at origin. The actual bit or bits in error are not necessarily identified. Therefore, although the bit set is known to contain one or more errors, the bit set itself, and thus the entire data, are not accurate at destination. The data might have to be retransmitted. Retransmission of the data results in costly, cumbersome operations. Further, even numbers of errors in a set of bits are not necessarily identifiable using current parity code methods. Therefore, the destination data can be undetectably corrupted. In addition, current LDPC decoding techniques are complex and costly.

Various embodiments of the inventive communications decoder of the present invention use error correcting codes and a simple, unique process to "urge" a measurement signal associated with a bit in error toward a measurement signal associated with the correct, original bit, thus improving the likelihood of identifying destination data that matches the data encoded at origin and significantly improving data accuracy at destination. The simple, unique process facilitates efficient implementations. The low overhead associated with the simple, unique process minimizes costs. LDPC decoding is far less complex by using the iterative communications decoder of the present invention.

Figure 7:
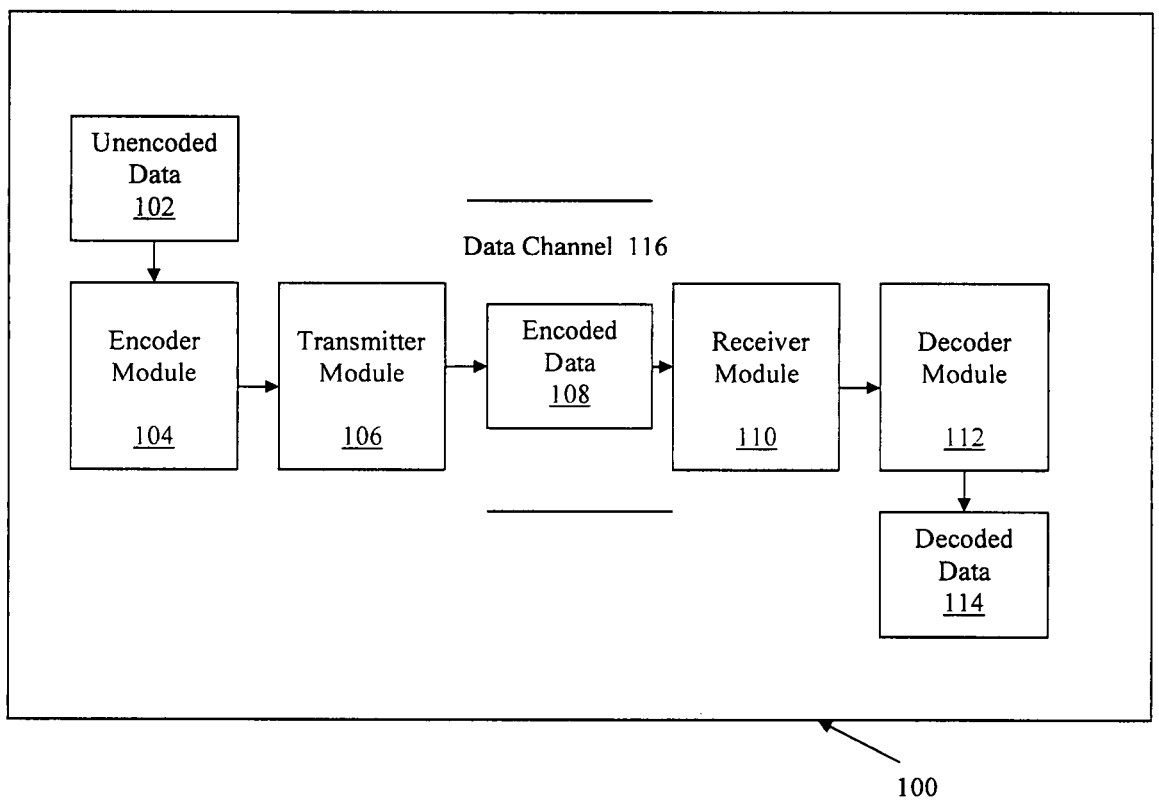
FIG. 7 is a system view of a communication environment including a decoder module, according to one embodiment.

FIG. 7 is a system view of a communication environment 100 including a decoder module 112, according to one embodiment. The communication environment 100 is associated with, for example, unencoded data 102, an encoder module 104, a transmitter module 106, encoded data 108, a receiver module 110, the decoder module 112, and decoded data 114.

Particularly, in the communication environment 100 of FIG. 7, unencoded data 102, or a portion of the unencoded data 102, is encoded by the encoder module 104. The transmitter module 106 transmits the encoded data 108 via data channel 116. The receiver module 110 receives the encoded data 108. The decoder module 112 decodes the encoded data 108 and generates decoded data 114. In various embodiments, various modules are implemented individually or integrated into a particular device or software. For example, the receiver module 110 and the decoder module 112 are integrated into a device such as a receiver and/or a software module. Further, various modules are fully or partially integrated with or implemented as hardware devices. For example, the transmitter module 106 is implemented as, or integrated with, a transmitter. In another example, the decoder module 112 is integrated as software, circuitry, or combinations thereof.

Generally, the decoder module 112 generates the decoded data 114 via variations of the following technique. For each bit set of the encoded data, a set of measured signals associated with the encoded data is rounded to the nearest most likely possible measurement if no noise were present, e.g., to a nearest transmission symbol, as further described with respect to FIG. 9B. The set of transmission symbols is converted into a set of hard code decision values. An error check is performed on the set of hard code decision values, as further described with respect to FIG. 9C. The set of measured signals is adjusted based on an outcome of the error check of the set of hard code decision values, as further described with respect to FIG. 9D. The foregoing is performed in passes across all measured signal sets of the encoded data until a predetermined stopping condition is met. A more detailed discussion follows.

Figure 8A:
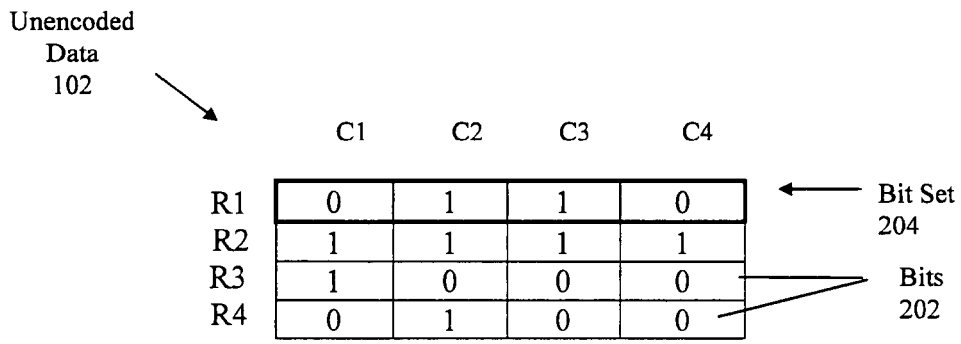
FIG. 8A is an illustration of unencoded data, according to one embodiment.

More particularly, FIG. 8A is an illustration of the unencoded data 102, according to one embodiment. The unencoded data 102 include all or a portion of datapoints associated with the unencoded data, represented in FIG. 8A as bits 202. Various embodiments include other representations.

Particularly, in FIG. 8A, the unencoded data 102 are grouped into subsets of datapoints, e.g., subsets of bits 202. Such subsets, of datapoints are sometimes referred to as "bit sets" 204. Bit sets 204 are unstructured or structured in various arrangements. Such arrangements include matrices, multidimensional hypercubes, and other geometries. To illustrate, the unencoded data 102 are shown as 16 bit sets 204 arranged in a two dimensional matrix having rows one through four (R1-R4, respectively) and columns one through four (C1-C4, respectively).

Figure 8B:
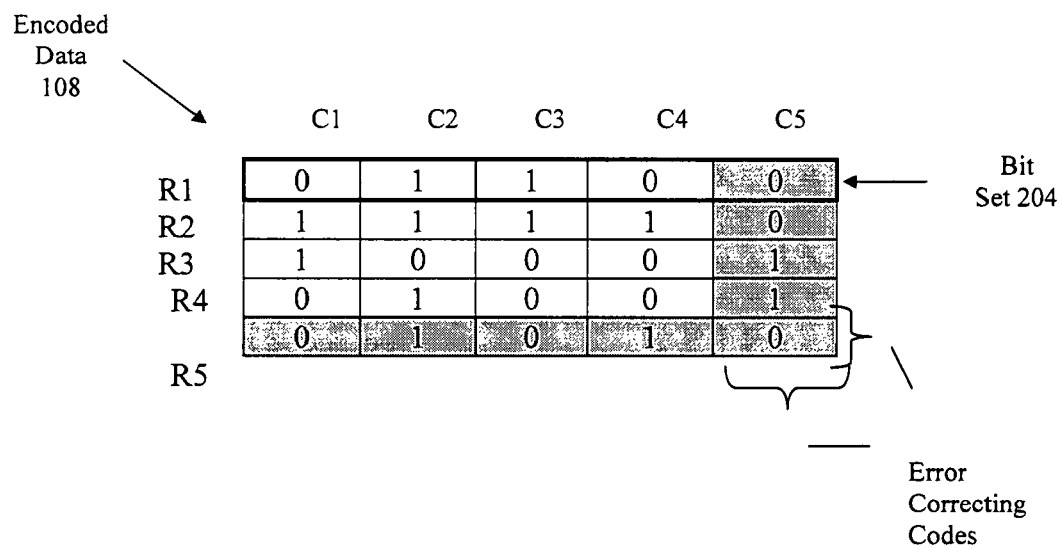
FIG. 8B is an illustration of encoded data, according to one embodiment.

FIG. 8B is an illustration of the encoded data 108. In general, the unencoded data 102 are encoded with one or more error correcting codes 206 to generate the encoded data 108. In one embodiment, an error correcting code 206 is generated for each bit set 204 of the unencoded data 102. The error correcting codes 206 include parity codes, Hamming codes, Golay codes, and other error correcting codes.

Particularly, in FIG. 8B, an error correcting code 206 such as a parity code is associated with, e.g., included in, each bit set 204 of the unencoded data 102, i.e., rows R1 through R4 and columns C1 through C4. For example, in row R1, column C5 an error correcting code 206 of "0" is associated with the bit set 204 of row R1 (even parity). In row R2, column C5 an error correcting code 206 of "0" is associated with the bit set 204 of row R2 (even parity). In row R5, column C1 an error correcting code 206 of "0" is associated with the bit set 204 of column 1 (even parity). In row R5, column C5 a code of "0" is associated with the bit sets 204 of row R5 and column C5 (parity on parity, even parity).

Figure 8C:
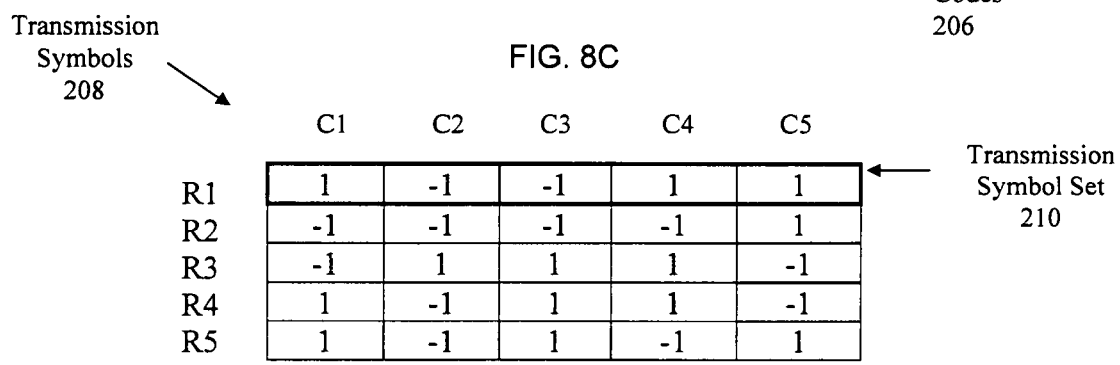
FIG. 8C is an illustration of transmission symbols, according to one embodiment.

FIG. 8C is an illustration of transmission symbols 208, according to one embodiment. Particularly, in FIG. 8C, the encoded data 108, e.g., the unencoded data 102 and the error correcting codes 206, are converted into the transmission symbols 208. One example of transmission symbols are signals modulated for transmission. The transmission symbols 208 are grouped into subsets of the transmission symbols 208, sometimes referred to as the transmission symbol sets 210. The transmission symbol sets 210 correspond to the bit sets 204 (FIG. 8B). For example, the transmission symbol set 210 at row one R1 corresponds to the bit set 204 at row one R1 (FIG. 8B).

Various methods convert and transmit the encoded data 108. For example, binary phase-shift keying (BPSK) is used to transmit the encoded data 108 over a radio channel. Each of the bits 202 is converted to a carrier phase of 0 degrees if the bit 202 is 0 or to a carrier phase of 180 degrees if the bit 202 is 1. This conversion corresponds to I=1 for bits of 0 and I=−1 for bits of 1, where the output signal is in the form of:

$$Vout = Itx * \cos(w*t),$$

where Itx is the baseband amplitude signal, w is the radial carrier frequency, t is time and Vout is the transmitted voltage. Other methods of conversion and transmission can be used including, for example, quaternary or quadriphase PSK (QPSK) or quadrature amplitude modulation (QAM).

The transmitted signals are received by the receiver module 110. The receiver module 110 measures the received signals. The measured signals are arranged according to the original, corresponding bits sets 204 of the encoded data 108.

FIG. 9A is an illustration of measured signals 302, according to one embodiment. Particularly, in FIG. 9A, each received signal corresponding to each transmission symbol 208 (FIG. 8B) can be measured. The measured signals 302 are grouped into subsets of the measured signals 302, sometimes referred to as measured signal sets 304. The measured signal sets 304 correspond to the transmission symbol sets 210 (FIG. 8C) and to the bits sets 204 (FIG. 8B). For example, the measured signal set at row one R1 corresponds to the transmission symbol set 210 at row one R1 (FIG. 8C) and to the bit set 204 at row one R1 (FIG. 8B).

FIG. 9B is an illustration of transmission symbols 208, according to one embodiment. Particularly, in FIG. 9B, the measured signals 302 (FIG. 9A) is rounded to the nearest possible measurement if no noise were present, e.g., to the nearest transmission symbol 208 of (1, −1). Thus, for example, "0.3" is rounded up to 1, −0.9 is rounded down to −1, and so forth. The transmission symbols 208 reflect the rounded values of the measured signals of 302 (FIG. 8B).

FIG. 9C is an illustration of hard code decision values 306, according to one embodiment. Particularly, in FIG. 9C, the transmission symbols 208 (FIG. 9B) are converted into hard code decision values 306. The hard code decision values 306 are grouped into subsets, sometimes referred to as hard code decision value sets 308. The hard code decision value sets 308 correspond to the transmission symbol sets 208 (FIG. 9B), to the measured signal sets 304 (FIG. 9A), to the transmission symbol sets 210 (FIG. 8C), and to the bits sets 204 (FIG. 8B).

More particularly, the transmission symbols 208 are converted to binary form (demodulated) to generate hard code decision values 306. For example a transmission symbol 208 of "1" is converted to a bit 202 of "0" and a transmission symbol 208 of "−1" is converted to a bit 202 of "1". The hard code decision value 306 at row one R1, column five C5 of "0" is also an error correcting code 206, i.e., parity code, for the hard code decision value set 308.

An error check is performed using the error correcting code 204 of the hard code decision value set 308. For example, the parity code "0" of row one R1, column five C5 (Figure C5) is used to determine if parity is even. In this example, even parity was set originally for row R1, and the parity check fails.

FIG. 9D is an illustration of adjusted measured signals 310, according to one embodiment. Particularly, in FIG. 9D, the measured signals 302 of a measured signal set 304 (FIG. 9A) are adjusted based on the outcome of the error check of the hard code decision value set 308 (FIG. 9C). The adjusted measured signals 310 are grouped into subsets, sometimes referred to as adjusted measured signals set 312. The adjusted measured signal sets 312 correspond to the measured signal set 304 (FIG. 9A), to the hard code decision value sets 308 (FIG. 9C), to the transmission symbol sets 210 (FIG. 8C), and to the bits sets 204 (FIG. 8B).

If the hard code decision value set 308 passes the error check, each measured signal 302 of the corresponding measured signal set 304 is adjusted by a predetermined delta toward its corresponding nearest possible measurement if no noise were present, e.g., to the transmission symbol 208 of (1, −1) nearest in value to the current measured signal.

If the hard code decision value set 308 fails the error check, each measured signal 302 of the corresponding measured signal set 304 is adjusted by a predetermined delta away from its corresponding nearest possible measurement if no noise were present, e.g., to the nearest transmission symbol 208 of (1, −1), as shown in FIG. 9B. In this example, the hard code decision value set 308 of FIG. 9C failed the error check. Each measured signal 302 of measured signal set 304 of row one R1 is adjusted by a predetermined delta of 0.05 away from its nearest possible measurement if no noise were present.

In several embodiments of the communications decoder, the predetermined delta is determined by simulation. The predetermined delta can vary with the iteration process and can be reduced or otherwise modified as convergence is achieved. In this respect, "convergence" refers to convergence of a particular measured signal on a single point during iterative adjustments to the particular measured signal, thus the associated parity errors begin to decrease. In this manner, accuracy of the decoded data increases.

For example, the predetermined delta is small enough to provide small but steady changes to a particular measured signal value until the measured signal value converges to a point where its associated parity errors begin to decrease.

In embodiments of the communications decoder, each measured signal has at least two associated error correcting codes to provide multiple opportunities for adjustment during, a single pass. For example, if the measured signal sets are arranged in a two-dimensional geometry, each measured signal has two associated error correcting codes. In a three-dimensional geometry, each measured signal has three associated error checking codes.

The preceding steps are performed iteratively in sequence for each measured signal set 304 of the encoded data 108 (FIG. 9A). Completion of the iterative sequence across all measured sets of the encoded data is sometimes referred to as a "pass". In a two-dimensional matrix, for example, where the data are grouped by row and column, the preceding steps are performed in sequence for each row and each column of the matrix to complete one pass.

Multiple passes can be performed to lower the probability of assignment of measured signals to a transmission value associated with a bit that does not correspond to the original bit. The multiple passes can be performed until predetermined stopping condition(s) are met. Depending on the delta, three or four passes can be sufficient to minimize the probability of error. In this manner, the communications decoder utilizes error detection correcting codes and a simple, iterative process to achieve highly accurate decoding results with minimal overhead and minimal cost.

In one embodiment of the communications decoder, the predetermined stopping condition includes convergence of the adjusted measured signals on their most likely transmitted value. In another embodiment, the passes are stopped when no further changes occur in the hard code decision values between passes. In still another embodiment, the predetermined stopping condition can be a preset number of passes. Another predetermined stopping condition is an internal check that indicates the encoded data has a high probability of being accurately decoded, e.g., a cyclic redundancy check (CRC) is performed on the decoded data. Other predetermined stopping conditions are also possible.

Various embodiments of the communications decoder use error correcting codes such as Hamming codes or Golay codes. Hamming codes and Golay codes typically encode each bit set with multiple parity codes. In this manner, an error check using the codes can identify a particular hard code decision value in error, including a magnitude of directional drive of a signal measurement in error.

Thus, in various embodiments of the communications decoder using Hamming codes or Golay codes, error check(s) are performed on each hard code decision value set according to standard Hamming code or Golay codes practices. The additional information given by error correction codes such as Hamming codes or Golay codes is used to drive the adjusted measurements of detected errors away from hard coded decision values and other bits toward hard coded decision values. The above-described process is performed against each measured signal set until a predetermined stopping condition is met. Although the number of codes per set of encoded data greatly increases with the use of Hamming codes or Golay codes and the overhead associated with the error checks increases, convergence occurs more quickly than with data encoded with simple parity bits (one parity bit per bit set).

Various embodiments are associated with QAM modulation, wherein a group of bits is associated with an I, Q coordinate pair. The above iteration sequence and multiple pass approach can still be applied. For example, the hard code decision value is associated with the closest desired I, Q pair to identify hard code decision values. The I, Q pair is modified to be driven closer to (upon a passed error check) or further from (upon a failed error check) a nearest desired measurement point. Each bit associated with an I,Q point drives that point as it be evaluated in the above iteration sequence. The above process can be generalized to multidimensional signal constellations, such as where QAM is used by two different polarizations in microwave radio systems to create a four dimensional received constellation point.

Figure 10:
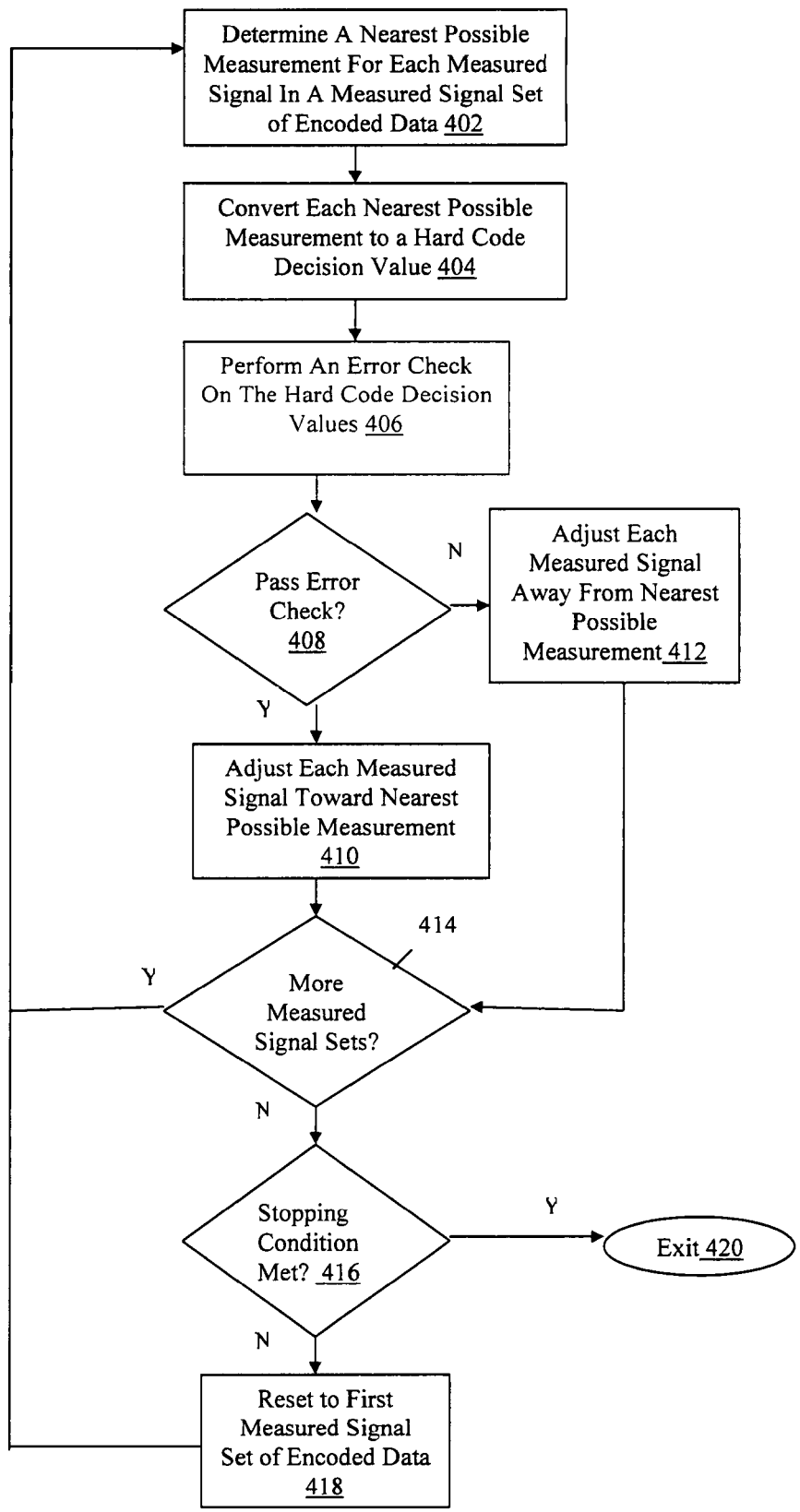
FIG. 10 is a flowchart of a method associated with decoding, according to one embodiment.

FIG. 10 is a flowchart of a method associated with decoding, according to one embodiment of the invention. Particularly, FIG. 10 includes a DETERMINE A NEAREST POSSIBLE MEASUREMENT FOR EACH MEASURED SIGNAL IN A MEASURED SIGNAL SET OF ENCODED DATA 402 operation. In the DETERMINE A NEAREST POSSIBLE MEASUREMENT FOR EACH MEASURED SIGNAL IN A MEASURED SIGNAL SET OF ENCODED DATA 402 operation, a nearest possible measurement if no noise were present is associated with each measured signal in a measured signal set, as previously discussed.

From the DETERMINE A NEAREST POSSIBLE MEASUREMENT FOR EACH MEASURED SIGNAL IN A MEASURED SIGNAL SET OF ENCODED DATA 402 operation, flow moves to a CONVERT EACH NEAREST POSSIBLE MEASUREMENT TO A HARD CODE DECISION VALUE 404 operation. In the CONVERT EACH NEAREST POSSIBLE MEASUREMENT TO A HARD CODE DECISION VALUE 404 operation, each nearest possible measurement associated with each measured signal in a measured signal set is converted to a corresponding hard code decision value, e.g., bit 1 or 0, as previously discussed.

From the CONVERT EACH NEAREST POSSIBLE MEASUREMENT TO A HARD CODE DECISION VALUE 404 operation, flow moves to a PERFORM AN ERROR CHECK ON THE HARD CODE DECISION VALUES 406 operation. In the PERFORM AN ERROR CHECK ON THE HARD CODE DECISION VALUES 406 operation, an error check is performed on the hard code decision value set, as previously discussed.

From the PERFORM AN ERROR CHECK ON THE HARD CODE DECISION VALUES 406 operation, flow moves to a PASS ERROR CHECK 408 operation. In the PASS ERROR CHECK 408 operation, a determination is made if the hard code decision value set passed the error check (a passed error check) or failed the error check (a failed error check).

Upon the passed error check, flow moves to an ADJUST EACH MEASURED SIGNAL TOWARD NEAREST POSSIBLE MEASUREMENT 410 operation. In the ADJUST EACH MEASURED SIGNAL TOWARD NEAREST POSSIBLE MEASUREMENT 410 operation, each measured signal of the measured signal set is adjusted toward the nearest possible measurement, as previously discussed.

Upon the failed error check, flow moves to an ADJUST EACH MEASURED SIGNAL AWAY FROM NEAREST. POSSIBLE MEASUREMENT 412 operation. In the ADJUST EACH MEASURED SIGNAL AWAY FROM NEAREST POSSIBLE MEASUREMENT 412 operation, each measured signal of the measured signal set is adjusted away from the nearest possible measurement, as previously discussed.

From either the ADJUST EACH MEASURED SIGNAL TOWARD NEAREST POSSIBLE MEASUREMENT 410 operation or the ADJUST EACH MEASURED SIGNAL AWAY FROM NEAREST POSSIBLE MEASUREMENT 412 operation, flow moves to a MORE MEASURED SIGNAL SETS 414 operation. In the MORE MEASURED SIGNAL SETS 414 operation, a determination is made as to whether more measured signal sets remain to be processed in the sequence, as previously discussed.

Upon a determination that more measured signal sets remain, flow returns to the DETERMINE A NEAREST POSSIBLE MEASUREMENT FOR EACH MEASURED SIGNAL IN A MEASURED SIGNAL SET OF ENCODED DATA 402 operation.

Upon a determination that no more measured signals sets remain, flow moves to a STOPPING CONDITION MET 416 operation. In the STOPPING CONDITION MET 416 operation, a determination is made whether a predetermined stopping condition is met, as previously discussed.

Upon a determination that a stopping condition is not met, flow moves to a RESET TO FIRST MEASURED SIGNAL SET OF ENCODED DATA 418 operation.

From the RESET TO FIRST MEASURED SIGNAL SET OF ENCODED DATA 418 operation, flow returns to the DETERMINE A NEAREST POSSIBLE MEASUREMENT FOR EACH MEASURED SIGNAL IN A MEASURED SIGNAL SET OF ENCODED DATA 402 operation.

Upon a determination that a stopping condition is met, flow exits in an EXIT 420 operation. In this manner, the decoding method utilizes error correcting codes and a simple, iterative process to achieve highly accurate decoding results.

Figure 11:
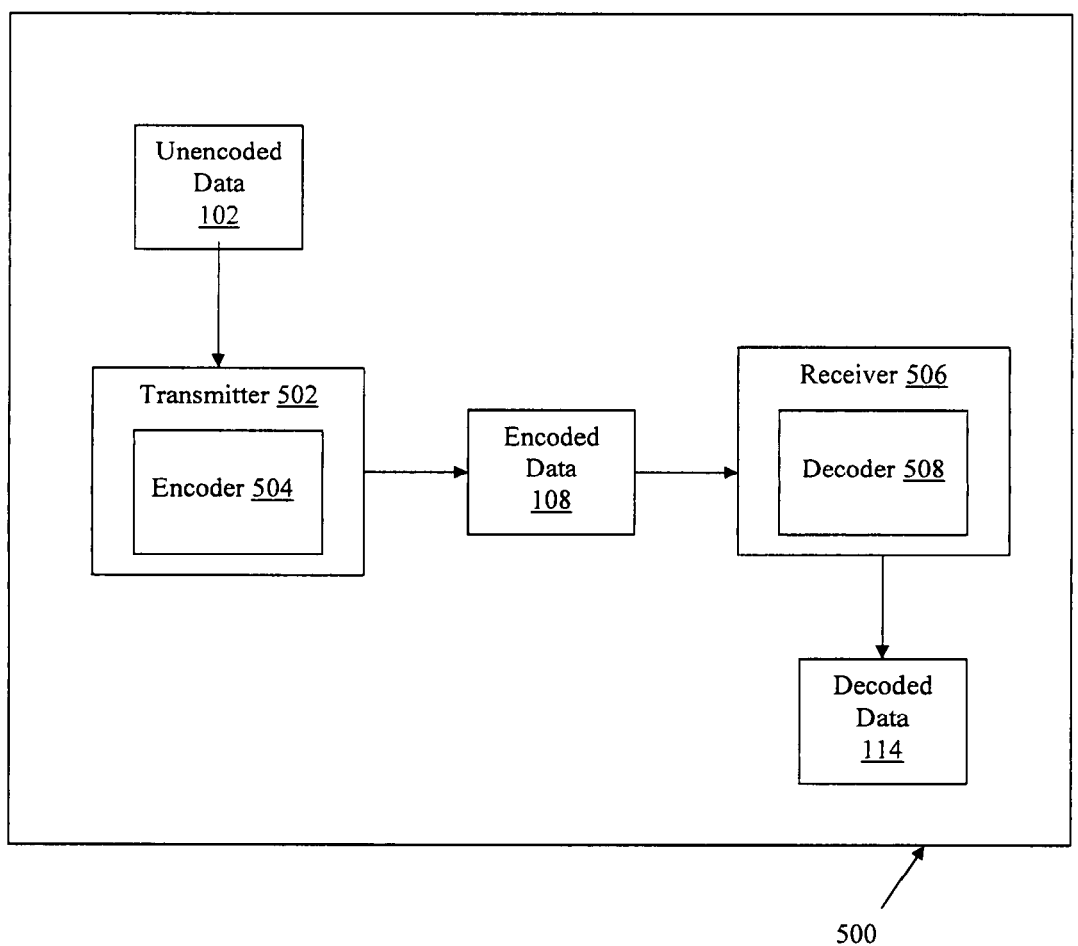
FIG. 11 is a schematic of a communication environment including a communications decoder, according to one embodiment.

FIG. 11 is a schematic of a communication environment 500, including a communications decoder 508, according to one embodiment. The communication environment 500 includes, for example, unencoded data 102, a transmitter 502, an encoder 504, encoded data 108, a receiver 506, the communications decoder 508, and decoded data 114. In various embodiments, various components are partially or wholly integrated. For example, the encoder 504 can be partially or wholly integrated with the transmitter 502. In another example, the communications decoder 508 can be partially or wholly integrated with the receiver 506. In various embodiments, the components can be implemented without co-integration. For example, the communications decoder 508 can be implemented as a stand-alone component.

As previously discussed, the encoder 504 encodes unencoded data 102, such as a collection of bits. The encoder 504 encodes the unencoded data 102 using error correcting codes (codes). The codes include parity codes, Hamming codes, Golay codes, and other codes, as previously discussed. In one embodiment, the encoder 504 encodes each set of bits in the unencoded data 102. The encoder 504 or the transmitter 502 transmits the encoded data 108. The encoded data can be transmitted as transmission symbols associated with analog signals, as previously discussed. The receiver 506 receives and measures the signals associated with the encoded data 108, as previously discussed.

The communications decoder 508 rounds each set of measured signals to the nearest possible measurement if no noise were present, e.g., to a nearest transmission symbol. The communications decoder 508 converts the set of transmission symbols to a set of hard code decision values. The communications decoder 508 performs an error check on the set of hard code decision values, using an error correcting code associated with the hard code decision values. The communications decoder 508 adjusts each measured signal in the set of measured signals based on an outcome of the error check of the set of hard code decision values. The communications decoder 508 performs the foregoing steps across all of the sets of measured signals, in multiple passes, until a predetermined stopping condition is met, resulting in decoded data 114. In this manner, the decoder utilizes error correcting codes and a simple, iterative process to achieve highly accurate decoding results.

Multidimensional parity codes operate at 2 dB Eb/No (4 db Eb/No, 6 db Eb/No) when decoded in the described manner at an error rate of $10^{-5}$. These codes operate at a rate of R=0.5 (50% message bits; 50% parity check bits).

In addition, it will be appreciated that the various operations, processes, and methods disclosed herein can be embodied in a machine-readable medium and/or a machine accessible medium compatible with a data processing System (e.g., a computer system), and can be performed in any order.

Forward Error Correction

In certain embodiments, the receiver is configured for use with an in vivo transmitter that employs FEC (Forward Error Correction) to provide additional gain to combat interference from other unwanted signals and noise. The error correction is simple in the transmitter and receiver, and provides high coding gain. This functionality is achieved using single parity check product codes and a novel SISO (Soft In Soft Out) iterative decoding algorithm.

The transmitter encodes the message by arranging it in rows and columns. Each row has an appended parity bit, and similarly each column has an appended parity bit. For example, a 100 bit message could be arranged in a 10 by 10 bit array. Parity bits would be added to create a final 11 by 11 bit array that would then be transmitted on the channel using BPSK. For additional gain, additional dimensions could be used, such as three if a cube were created to arrange the message and parity bits.

The receiver decodes the message by an iterative process to achieve high coding gain. Each bit is sampled and saved in "soft" form. Assuming ideal samples (i.e., hard decision points) are normalized to −1 and +1, received bits would come in a range between say, −2.0 and +2.0. A hard decision is made on all samples and parity checked. If a row or column has a parity error, the samples of that row or column are repulsed from their corresponding hard decision point by a small delta. If the row or column has no parity error, the samples of that row or column are attracted to their corresponding hard decision point by a small delta. Using a properly selected delta, based on expected channel SNR (Signal to Noise Ratio), ten iterations is usually sufficient to achieve an 8 to 10 dB coding gain on AWGN (Additive White Gaussian Noise). This method is easy to implement in stored program DSP or FPGA/ASIC logic. It also comes within one or two dB of the Shannon limit for forward error correction given the particular coding rate.

Noise Canceling Receiver

In certain embodiments, signals from in vivo transmitter devices and noise signals are maximized in different orientations. This scenario permits using noise cancellation techniques to subtract the noise signal from the pill signal, to significantly enhance SNR (Signal to Noise Ratio). For example, it has been observed that skin probes placed laterally (side to side) over the stomach pick-up greater pill signals, while probes placed longitudinally (head to toe) over the stomach pick-up greater external noise sources. The subtraction process uses adaptive digital filters on two sets of probes (one pair lateral, and one pair longitudinal) to greatly enhance SNR. The details of this noise cancellation algorithm are well known and often use Widrow's LMS (Least Mean Squares) adaptation algorithm, although many others can also be used. As such, in certain embodiments noise canceling technology is employed to receive volume conduction sources that have low signal strength and high noise backgrounds.

Systems

In certain embodiments, the signal receivers are part of a body associated system or network of sensors, receivers, and optionally other devices, both internal and external, which provide a variety of different types of information that is ultimately collected and processed by a processor, such as an external processor, which then can provide contextual data about a patient as output. For example that sensor may be a member of an in-body network of devices which can provide an output that includes data about pill ingestion, one or more physiological sensed parameters, implantable device operation, etc., to an external collector of the data. The external collector, e.g., in the form of a health care network server, etc., of the data then combines this receiver provided data with additional relevant data about the patient, e.g., weight, weather, medical record data, etc., and may process this disparate data to provide highly specific and contextual patient specific data.

Systems of the subject invention include, in certain embodiments, a signal receiver and one or more pharma-informatics enabled active agent containing compositions. The pharma-informatics enabled pharmaceutical composition is an active agent-containing composition having an identifier stably associated therewith. In certain embodiments, the compositions are disrupted upon administration to a subject. As such, in certain embodiments, the compositions are physically broken, e.g., dissolved, degraded, eroded, etc., following delivery to a body, e.g., via ingestion, injection, etc. The compositions of these embodiments are distinguished from devices that are configured to be ingested and survive transit through the gastrointestinal tract substantially, if not completely, intact. The compositions include an identifier and an active agent/carrier component, where both of these components are present in a pharmaceutically acceptable vehicle.

The identifiers of the compositions may vary depending on the particular embodiment and intended application of the composition so long as they are activated (i.e., turned on) upon contact with a target physiological location, e.g., stomach. As such, the identifier may be an identifier that emits a signal when it contacts a target body (i.e., physiological) site. In addition or alternatively, the identifier may be an identifier that emits a signal when interrogated after it has been activated. The identifier may be any component or device that is capable of providing a detectable signal following activation, e.g., upon contact with the target site. In certain embodiments, the identifier emits a signal once the composition comes into contact with a physiological target site, e.g., as summarized above. For example, a patient may ingest a pill that, upon contact with the stomach fluids, generates a detectable signal.

The compositions include an active agent/carrier component. By "active agent/carrier component" is meant a composition, which may be a solid or fluid (e.g., liquid), which has an amount of active agent, e.g., a dosage, present in a pharmaceutically acceptable carrier. The active agent/carrier component may be referred to as a "dosage formulation."

"Active agent" includes any compound or mixture of compounds which produces a physiological result, e.g., a beneficial or useful result, upon contact with a living organism, e.g., a mammal, such as a human. Active agents are distinguishable from such components as vehicles, carriers, diluents, lubricants, binders and other formulating aids, and encapsulating or otherwise protective components. The active agent may be any molecule, as well as binding portion or fragment thereof, that is capable of modulating a biological process in a living subject. In certain embodiments, the active agent may be a substance used in the diagnosis, treatment, or prevention of a disease or as a component of a medication. In certain embodiments, the active agent may be a chemical substance, such as a narcotic or hallucinogen, which affects the central nervous system and causes changes in behavior.

The active agent (i.e., drug) is capable of interacting with a target in a living subject. The target may be a number of different types of naturally occurring structures, where targets of interest include both intracellular and extracellular targets. Such targets may be proteins, phospholipids, nucleic acids and the like, where proteins are of particular interest. Specific proteinaceous targets of interest include, without limitation, enzymes, e.g. kinases, phosphatases, reductases, cyclooxygenases, proteases and the like, targets comprising domains involved in protein-protein interactions, such as the SH2, SH3, PTB and PDZ domains, structural proteins, e.g.

actin, tubulin, etc., membrane receptors, immunoglobulins, e.g. IgE, cell adhesion receptors, such as integrins, etc, ion channels, transmembrane pumps, transcription factors, signaling proteins, and the like.

The active agent (i.e., drug) may include one or more functional groups necessary for structural interaction with the target, e.g., groups necessary for hydrophobic, hydrophilic, electrostatic or even covalent interactions, depending on the particular drug and its intended target. Where the target is a protein, the drug moiety may include functional groups necessary for structural interaction with proteins, such as hydrogen bonding, hydrophobic-hydrophobic interactions, electrostatic interactions, etc., and may include at least an amine, amide, sulfhydryl, carbonyl, hydroxyl or carboxyl group, such as at least two of the functional chemical groups.

Drugs of interest may include cyclical carbon or heterocyclic structures and/or aromatic or polyaromatic structures substituted with one or more of the above functional groups. Also of interest as drug moieties are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The drugs may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the drug may be obtained from a library of naturally occurring or synthetic molecules; including a library of compounds produced through combinatorial means, i.e., a compound diversity combinatorial library. When obtained from such libraries, the drug moiety employed will have demonstrated some desirable activity in an appropriate screening assay for the activity. Combinatorial libraries, as well as methods for producing and screening such libraries, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; etc.

As summarized above, the compositions of the invention further include a pharmaceutically acceptable vehicle (i.e., carrier). Common carriers and excipients, such as corn starch or gelatin, lactose, dextrose, sucrose, microcrystalline cellulose, kaolin, mannitol, dicalcium phosphate, sodium chloride, and alginic acid are of interest. Disintegrators commonly used in the formulations of the invention include croscarmellose, microcrystalline cellulose, corn starch, sodium starch glycolate and alginic acid.

Further details about embodiments of pharma-informatics enabled pharmaceutical compositions may be found in pending PCT application PCT/US2006/16370 titled "Pharma-Informatics System" and filed on Apr. 28, 2006; as well as U.S. Provisional Application. Ser. Nos. 60/807,060 titled "Acoustic Pharma-Informatics System" filed on Jul. 11, 2006; 60/862,925 titled "Controlled Activation Pharma-Informatics System," filed on Oct. 25, 2006; and 60/866,581 titled "In-Vivo Transmission Decoder," filed on Nov. 21, 2006; the disclosures of which are herein incorporated by reference.

In certain embodiments the systems include an external device which is distinct from the receiver (which may be implanted or topically applied in certain embodiments), where this external device provides a number of functionalities. Such an apparatus can include the capacity to provide feedback and appropriate clinical regulation to the patient. Such a device can take any of a number of forms. By example, the device can be configured to sit on the bed next to the patient, e.g., a bedside monitor. Other formats include, but are not limited to, PDAs, smart phones, home computers, etc. The device can read out the information described in more detail in other sections of the subject patent application, both from pharmaceutical ingestion reporting and from physiological sensing devices, such as is produced internally by a pacemaker device or a dedicated implant for detection of the pill. The purpose of the external apparatus is to get the data out of the patient and into an external device. One feature of the external apparatus is its ability to provide pharmacologic and physiologic information in a form that can be transmitted through a transmission medium, such as a telephone line, to a remote location such as a clinician or to a central monitoring agency.

Systems of the invention enable a dynamic feedback and treatment loop of tracking medication timing and levels, measuring the response to therapy, and recommending altered dosing based on the physiology and molecular profiles of individual patients. For example, a symptomatic heart failure patient takes multiple drugs daily, primarily with the goal of reducing the heart's workload and improving patient quality of life. Mainstays of therapy include angiotensin converting enzyme (ACE) inhibitors, β-blockers and diuretics. For pharmaceutical therapy to be effective, it is vital that patients adhere to their prescribed regimen, taking the required dose at the appropriate time. Multiple studies in the clinical literature demonstrate that more than 50% of Class II and III heart failure patients are not receiving guideline-recommended therapy, and, of those who are titrated appropriately, only 40-60% adhere to the regimen. With the subject systems, heart failure patients can be monitored for patient adherence to therapy, and adherence performance can be linked to key physiologic measurements, to facilitate the optimization of therapy by physicians.

In certain embodiments, the systems of the invention may be employed to obtain an aggregate of information that includes sensor data and administration data. For example, one can combine the heart rate, the respiration rate, multi-axis acceleration data, something about the fluid status, and something about temperature, and derive indices that will inform about the total activity of the subject, that can be used to generate a physiological index, such as an activity index. For instance, when there is a rise in temperature, heart rate goes up a bit, and respiration speeds up, which may be employed as an indication that the person is being active. By calibrating this, the amount of calories the person is burning at that instant could be determined. In another example, a particular rhythmic set of pulses or multi-axis acceleration data can indicate that a person is walking up a set of stairs, and from that one can infer how much energy they are using. In another embodiment, body fat measurement (e.g. from impedance data) could be combined with an activity index generated from a combination of measured biomarkers to generate a physiological index useful for management of a weight loss or cardiovascular health program. This information can be combined with cardiac performance indicators to get a good picture of overall health, which can be combined with pharmaceutical therapy administration data. In another embodiment, one might find for example that a particular pharmaceutical correlates with a small increase in body temperature, or a change in the electrocardiogram. One can develop a pharmacodynamic model for the metabolism of the drug, and use the information from the receiver to essentially fit the free parameters in that model to give much more accurate estimation of the levels actually present in the serum of the subject. This information could be fed back to dosing regimes. In another embodiment, one can combine information from a sensor that measures uterine contractions (e.g. with a strain gauge) and that also monitors fetal heart rate, for use as a high-risk pregnancy monitor.

In certain embodiments, the subject specific information that is collected using the systems of the invention may be transmitted to a location where it is combined with data from one or more additional individuals to provide a collection of data which is a composite of data collected from 2 or more, e.g., 5 or more, 10 or more, 25 or more, 50 or more, 100 or more, 1000 or more, etc., individuals. The composite data can then be manipulated, e.g., categorized according to different criteria, and made available to one or more different types of groups, e.g., patient groups, health care practitioner groups, etc., where the manipulation of data may be such as to limit the access of any given group to the type of data that group can access. For example, data can be collected from 100 different individuals that are suffering from the same condition and taking the same medication. The data can be processed and employed to develop easy to follow displays regarding patient compliance with a pharmaceutical dosage regimen and general health. Patient members of the group can access this information and see how their compliance matches with other patient members of the group, and whether they are enjoying the benefits that others are experiencing. In yet another embodiment, doctors can also be granted access to a manipulation of the composite data to see how their patients are matching up with patients of other doctors, and obtain useful information on how real patients respond to a given therapeutic treatment regiment. Additional functionalities can be provided to the groups given access to the composite data, where such functionalities may include, but are not limited to: ability to annotate data, chat functionalities, security privileges, etc.

Computer Readable Media & Programming

In certain embodiments, the system further includes an element for storing data, i.e., a data storage element, where this element is present on an external device, such as a bedside monitor, PDA, smart phone, etc. Typically, the data storage element is a computer readable medium. The term "computer readable medium" as used herein refers to any storage or transmission medium that participates in providing instructions and/or data to a computer for execution and/or processing. Examples of storage media include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information may be "stored" on computer readable medium, where "storing" means recording information such that it is accessible and retrievable at a later date by a computer. With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

The invention also provides computer executable instructions (i.e., programming) for performing the above methods. The computer executable instructions are present on a computer readable medium. Accordingly, the invention provides a computer readable medium containing programming for use in detecting and processing a signal generated by a composition of the invention, e.g., as reviewed above.

As such, in certain embodiments the systems include one or more of: a data storage element, a data processing element, a data display element, data transmission element, a notification mechanism, and a user interface. These additional elements may be incorporated into the receiver and/or present on an external device, e.g., a device configured for processing data and making decisions, forwarding data to a remote location which provides such activities, etc.

The above described systems are reviewed in terms of communication between an identifier on a pharmaceutical composition and a receiver. However, the systems are not so limited. In a broader sense, the systems are composed of two or more different modules that communicate with each other, e.g., using the transmitter/receiver functionalities as reviewed above, e.g., using the monopole transmitter (e.g., antenna) structures as described above. As such, the above identifier elements may be incorporated into any of a plurality of different devices, e.g., to provide a communications system between two self-powered devices in the body, where the self-powered devices may be sensors, data receivers and storage elements, effectors, etc. In an exemplary system, one of these devices may be a sensor and the other may be a communication hub for communication to the outside world. This inventive embodiment may take a number of forms. There can be many sensors, many senders and one receiver. They can be transceivers so both of these can take turns sending and receiving according to known communication protocols. In certain embodiments, the means of communication between the two or more individual devices is the mono polar system, e.g., as described above. In these embodiments, each of these senders may be configured to take turns sending a high frequency signal into the body using a monopole pulling charge into and out of the body which is a large capacitor and a conductor. The receiver, a monopole receiver is detecting at that frequency the charge going into and out of the body and decoding an encrypted signal such as an amplitude modulated signal or frequency modulated signal. This embodiment of the present invention has broad uses. For example, multiple sensors can be placed and implanted on various parts of the body that measure position or acceleration. Without having wires connecting to a central hub, they can communicate that information through a communication medium.

Receiver Fabrication

As reviewed above, in certain embodiments of interest; the receiver element includes a semiconductor support component. Any of a variety of different protocols may be employed in manufacturing the receiver structures and components thereof. For example, molding, deposition and material removal, e.g., planar processing techniques, such as Micro-Electro-Mechanical Systems (MEMS) fabrication techniques, including surface micromachining and bulk micromachining techniques, may be employed. Deposition techniques that may be employed in certain embodiments of fabricating the structures include, but are not limited to: electroplating, cathodic arc deposition, plasma spray, sputtering, e-beam evaporation, physical vapor deposition, chemical vapor deposition, plasma enhanced chemical vapor deposition, etc. Material removal techniques included, but are not limited to: reactive ion etching, anisotropic chemical etching, isotropic chemical etching, planarization, e.g., via chemical mechanical polishing, laser ablation, electronic discharge machining (EDM), etc. Also of interest are lithographic protocols. Of interest in certain embodiments is the use of planar processing protocols, in which structures are built up and/or removed from a surface or surfaces of an initially planar substrate using a variety of different material removal and deposition protocols applied to the substrate in a sequential manner. Illustrative fabrication methods of interest are described in greater detail in copending PCT application serial no. PCT/US2006/016370; the disclosure of which is herein incorporated by reference.

In certain embodiments, off-the-shelf components may be employed to fabricate the receivers. For example, an off-the-shelf instrumentation amplifier for the input amp may be employed, e.g., in bare die form. Custom logic, either in an FPGA or in an ASIC, that handles the demodulator, the memory, the microprocessor functions, and all the interface functions may be used. The transmitter may be an off-the-shelf chip, e.g., made by Zarlink, in the mixed communication band, which is approved for medical implants. The clock may be a stand-alone clock, or the device may have a microprocessor that has a clock built in.

Methods

In methods of invention, a signal is first transmitted from an in vivo transmitter, such as a pharma-informatics enabled composition. The transmitted signal is then received by the receiver, where it may be stored to a memory, retransmitted to another receiver, output to a user, e.g., either directly or via a third device, e.g., an external PDA, etc.

In the methods of the subject invention in which the in vivo transmitter is a pharma-informatics enabled composition, an effective amount of a composition of the invention is administered to a subject in need of the active agent present in the composition, where "effective amount" means a dosage sufficient to produce the desired result, e.g. an improvement in a disease condition or the symptoms associated therewith, the accomplishment of a desired physiological change, etc. The amount that is administered may also be viewed as a therapeutically effective amount. A "therapeutically effective amount" means the amount that, when administered to a subject for treating a disease, is sufficient to effect treatment for that disease.

The composition may be administered to the subject using any convenient means capable of producing the desired result, where the administration route depends, at least in part, on the particular format of the composition, e.g., as reviewed above. As reviewed above, the compositions can be formatted into a variety of formulations for therapeutic administration, including but not limited to solid, semi solid or liquid, such as tablets, capsules, powders, granules, ointments, solutions, suppositories and injections. As such, administration of the compositions can be achieved in various ways, including, but not limited to: oral, buccal, rectal, parenteral, intraperitoneal, intradermal, transdermal, intracheal, etc., administration. In pharmaceutical dosage forms, a given composition may be administered alone or in combination with other pharmaceutically active compounds, e.g., which may also be compositions having signal generation elements stably associated therewith.

The subject methods find use in the treatment of a variety of different conditions, including disease conditions. The specific disease conditions treatable by with the subject compositions are as varied as the types of active agents that can be present in the subject compositions. Thus, disease conditions include, but are not limited to: cardiovascular diseases, cellular proliferative diseases, such as neoplastic diseases, autoimmune diseases, hormonal abnormality diseases, infectious diseases, pain management, and the like.

By treatment is meant at least an amelioration of the symptoms associated with the disease condition afflicting the subject, where amelioration is used in a broad sense to refer to at least a reduction in the magnitude of a parameter, e.g. symptom, associated with the pathological condition being treated. As such, treatment also includes situations where the pathological condition, or at least symptoms associated therewith, are completely inhibited, e.g. prevented from happening, or stopped, e.g. terminated, such that the subject no longer suffers from the pathological condition, or at least the symptoms that characterize the pathological condition. Accordingly, "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). For the purposes of this invention, a "disease" includes pain.

A variety of subjects are treatable according to the present methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In representative embodiments, the subjects will be humans.

In certain embodiments, the subject methods, as described above, are methods of managing a disease condition, e.g., over an extended period of time, such as 1 week or longer, 1 month or longer, 6 months or longer, 1 year or longer, 2 years or longer, 5 years or longer, etc. The subject methods may be employed in conjunction with one or more additional disease management protocols, e.g., electrostimulation based protocols in cardiovascular disease management, such as pacing protocols, cardiac resynchronization protocols, etc; lifestyle, such a diet and/or exercise regimens for a variety of different disease conditions; etc.

In certain embodiments, the methods include modulating a therapeutic regimen based data obtained from the compositions. For example, data may be obtained which includes information about patient compliance with a prescribed therapeutic regimen. This data, with or without additional physiological data, e.g., obtained using one or more sensors, such as the sensor devices described above, may be employed; e.g., with appropriate decision tools as desired, to make determinations of whether a given treatment regimen should be maintained or modified in some way, e.g., by modification of a medication regimen and/or implant activity regimen. As such, methods of invention include methods in which a therapeutic regimen is modified based on signals obtained from the composition(s).

In certain embodiments, also provided are methods of determining the history of a composition of the invention; where the composition includes an active agent, an identifier element and a pharmaceutically acceptable carrier. In certain embodiments where the identifier emits a signal in response to an interrogation, the identifier is interrogate, e.g., by a wand or other suitable interrogation device, to obtain a signal. The obtained signal is then employed to determine historical information about the composition, e.g., source, chain of custody, etc.

In yet other embodiments where the identifier is one that survives digestion, the methods generally include obtaining the signal generation element of the composition, e.g., by retrieving it from a subject that has ingested the composition, and then determining the history of the composition from obtained signal generation element. For example, where the signal, generation element includes an engraved identifier, e.g., barcode or other type of identifier, the engraved identifier may be retrieved from a subject that has ingested the composition and then read to identify at least some aspect of the history of the composition, such as last known purchaser, additional purchasers in the chain of custody of the composition, manufacturer, handling history, etc. In certain embodiments, this determining step may include accessing a database or analogous compilation of stored history for the composition.

Utility

Medical embodiments of the present invention provide the clinician an important new tool in their therapeutic armamentarium: automatic detection and identification of pharmaceutical agents actually delivered into the body. The applications of this new information device and system are multi-fold. Applications include, but are not limited to: (1) monitoring patient compliance with prescribed therapeutic regimens; (2) tailoring therapeutic regimens based on patient compliance; (3) monitoring patient compliance in clinical trials; (4) monitoring usage of controlled substances; and the like. Each of these different illustrative applications is reviewed in greater detail below in copending PCT Application Serial No. PCT/US2006/016370; the disclosure of which is herein incorporated by reference. Additional applications in which the subject receivers find use include, but are not limited to: U.S. provisional Application Ser. Nos. 60/887,780 titled "Signal Receivers For Pharma-Informatics Systems," and filed on Feb. 1, 2007; 60/956,694 titled "Personal Health Signal Receivers," and filed on Aug. 18, 2007 and 60/949,223 titled "Ingestible Event Marker;" and filed on Jul. 11, 2007, the disclosures of which applications are incorporated herein by reference.

Kits

Also provided are kits for practicing the subject methods. Kits may include one or more receivers of the invention, as described above. In addition, the kits may include one or more dosage compositions, e.g., pharma-informatics enabled dosage compositions. The dosage amount of the one or more pharmacological agents provided in a kit may be sufficient for a single application or for multiple applications. Accordingly, in certain embodiments of the subject kits a single dosage amount of a pharmacological agent is present and in certain other embodiments multiple dosage amounts of a pharmacological agent may be present in a kit. In those embodiments having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit is dictated by the particular pharmacological agent employed, as describe above, e.g., the particular form of the agent such as whether the pharmacological agent is formulated into preparations in solid, semi solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperitoneal, intradermal, transdermal, intracheal, etc. Accordingly, certain systems may include a suppository applicator, syringe, I.V. bag and tubing, electrode, etc.

In certain embodiments, the kits may also include an external monitor device, e.g., as described above, which may provide for communication with a remote location, e.g., a doctor's office, a central facility etc., which obtains and processes data obtained about the usage of the composition.

In certain embodiments, the kits may include a smart parenteral delivery system that provides specific identification and detection of parenteral beneficial agents or beneficial agents taken into the body through other methods, for example, through the use of a syringe, inhaler, or other device that administers medicine, such as described in copending application Ser. No. 60/819,750; the disclosure of which is herein incorporated by reference.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, not intended to be limited to the exemplary embodiments shown and herein. Rather, the scope and spirit of present invention is embodied by the appended claims.

What is claimed is:

1. A signal receiver, comprising:
   (a) a receiver module configured to receive an encoded signal from an in vivo transmitter in a low signal to noise ratio (SNR) environment, the receiver module comprising:
      a first demodulator to receive the encoded signal and to produce a filtered complex baseband signal;
      a carrier frequency detector to receive the filtered complex baseband signal and generate an estimated carrier offset frequency;
      a second demodulator to receive the complex baseband signal and the estimated carrier offset frequency and to produce a demodulated encoded signal; and
   (b) a decoder module coupled to the receiver module to receive the demodulated encoded signal, the decoder module configured to decode the demodulated encoded signal with substantially no error; wherein the signal receiver is sized to be stably associated with a living subject in a manner that does not substantially impact movement of the living subject,
   wherein the first demodulator comprises:
   a first mixer;
   a direct digital synthesizer coupled to the first mixer to produce a nominal carrier frequency, wherein the received encoded signal is mixed by the mixer with the nominal carrier frequency to produce the complex baseband signal; and
   a first low pass filter coupled to the first mixer to filter the complex baseband signal.

2. The signal receiver according to claim 1, further comprising a decimation block coupled to the first low pass filter.

3. A signal receiver, comprising:
   (a) a receiver module configured to receive an encoded signal from an in vivo transmitter in a low signal to noise ratio (SNR) environment, the receiver module comprising:
      a first demodulator to receive the encoded signal and to produce a complex baseband signal;
      a carrier frequency detector to receive the filtered complex baseband signal and generate an estimated carrier offset frequency;
      a second demodulator to receive the complex baseband signal and the estimated carrier offset frequency and to produce a demodulated encoded signal; and
   (b) a decoder module coupled to the receiver module to receive the demodulated encoded signal, the decoder module configured to decode the demodulated encoded signal with substantially no error; wherein the signal receiver is sized to be stably associated with a living subject in a manner that does not substantially impact movement of the living subject,
   wherein the second demodulator comprises:
   a second mixer to mix the filtered complex baseband signal with the estimated carrier offset frequency; and
   a second low pass filter coupled to the second mixer to produce the demodulated encoded signal.

* * * * *